US012616601B2

(12) United States Patent
Sommer et al.

(10) Patent No.: US 12,616,601 B2
(45) Date of Patent: May 5, 2026

(54) HARNESS ASSEMBLY FOR USE WITH PATIENT TRANSPORT APPARATUSES

(71) Applicant: Stryker Corporation, Kalamazoo, MI (US)

(72) Inventors: Bradley Sommer, Lagrange, OH (US); Annali Evling, Portage, MI (US); Justin Jon Raymond, Jackson, MI (US)

(73) Assignee: Stryker Corporation, Portage, MI (US)

( * ) Notice: Subject to any disclaimer, the term of this patent is extended or adjusted under 35 U.S.C. 154(b) by 457 days.

(21) Appl. No.: 18/119,319

(22) Filed: Mar. 9, 2023

(65) Prior Publication Data
US 2023/0285176 A1 Sep. 14, 2023

Related U.S. Application Data

(60) Provisional application No. 63/318,092, filed on Mar. 9, 2022.

(51) Int. Cl.
*A61F 5/37* (2006.01)

(52) U.S. Cl.
CPC ................................. *A61F 5/3792* (2013.01)

(58) Field of Classification Search
CPC . A61F 5/3792; A47B 39/10; B60R 2021/022; B60R 2022/006
USPC ................................. 297/464, 476, 479, 482
See application file for complete search history.

(56) References Cited

U.S. PATENT DOCUMENTS

| | | | | | |
|---|---|---|---|---|---|
| 3,695,697 | A | * | 10/1972 | Stoffel | B60R 22/19 |
| | | | | | 297/483 |
| 4,323,204 | A | * | 4/1982 | Takada | B60R 22/1855 |
| | | | | | 242/381.4 |
| 5,160,186 | A | * | 11/1992 | Lee | B60R 22/30 |
| | | | | | 297/484 |
| 5,398,997 | A | * | 3/1995 | McFalls | B60R 22/357 |
| | | | | | 297/484 |
| 6,648,343 | B2 | * | 11/2003 | Way | A61G 5/061 |
| | | | | | 280/5.22 |
| 7,347,494 | B2 | * | 3/2008 | Boyle | B60N 2/2812 |
| | | | | | 297/254 |
| 8,960,804 | B2 | * | 2/2015 | Knight | B60N 2/2812 |
| | | | | | 297/484 |

(Continued)

FOREIGN PATENT DOCUMENTS

DE 3445822 A1 * 9/1986

*Primary Examiner* — Jose V Chen
(74) *Attorney, Agent, or Firm* — Howard & Howard Attorneys PLLC

(57) ABSTRACT

A harness assembly for use with a patient transport apparatus is provided. The harness assembly includes a strap for securing a patient to the patient transport apparatus. The harness assembly also includes a guard configured for removable attachment to the strap, the guard including a base, a keeper, and a retainer. The base defines a channel arranged to receive the strap. The keeper is arranged for movement relative to the base between a released position to permit movement of the strap along the channel of the base, and a secured position to restrict movement of the strap out of the channel. The retainer is coupled between the base and the keeper and is operable between an engaged configuration to retain the keeper in the secured position, and a disengaged configuration to permit movement of the keeper between the secured position and the released position.

20 Claims, 19 Drawing Sheets

(56)     References Cited

U.S. PATENT DOCUMENTS

| | | | |
|---|---|---|---|
| 2006/0138851 A1* | 6/2006 | Stoll .................... | B60N 2/2839 |
| | | | 297/464 |
| 2007/0182234 A1* | 8/2007 | Gruninger ............... | B60R 22/00 |
| | | | 297/464 |
| 2013/0341993 A1* | 12/2013 | Kennington .......... | B60R 22/105 |
| | | | 297/464 |
| 2015/0307061 A1* | 10/2015 | Chekaev ................. | B60R 22/12 |
| | | | 297/483 |
| 2021/0196535 A1 | 7/2021 | Brosnan et al. | |
| 2024/0225929 A1* | 7/2024 | Tumavich, Jr. ........ | A61G 5/066 |

\* cited by examiner

304;
SCRD;
306;
312

312

308;
RCV

312

302

300;
300C

314

306;
ENGD;
314

314

204;
206;
218;
220;
240;
244

308;
RCV

302

304;
RLSD

300;
300C

306;
DENGD

310

204;
206;
218;
220;
240;
244

HARNESS ASSEMBLY FOR USE WITH PATIENT TRANSPORT APPARATUSES

CROSS-REFERENCE TO RELATED APPLICATION

The subject patent application claims priority to and all the benefits of U.S. Provisional Patent Application No. 63/318,092 filed on Mar. 9, 2022 the disclosure of which is hereby incorporated by reference in its entirety.

BACKGROUND

In many instances, patients with limited mobility may be transported on one or more types of patient transport apparatuses, such as cots, hospital beds, stretchers, backboards, and the like. In certain situations, the patient may need to be restrained or otherwise secured to a patient support surface defined by the patient transport apparatus via one or more harness assemblies, straps, and the like. Those having ordinary skill in the art will appreciate that conventional patient restraints help limit relative movement between the patient and the patient support surface, and can help facilitate improved ease of transport for caregivers.

Typically, caregivers will secure the patient to the patient support surface using an arrangement of straps, harnesses, and the like, which may be adjustable to conform to different patient body types. As such, these conventional straps tend to be of excess length to allow usage with patients of a variety of body types. However, when these conventional straps are used with certain types of patients (e.g., shorter or younger patients), they can include an excess length and be difficult to manage, especially during patient transport.

A harness assembly that addresses one or more of the aforementioned challenges is desired.

SUMMARY

A harness assembly for use with a patient transport apparatus is provided. The harness assembly comprises: a strap for securing a patient to the patient transport apparatus, the strap defining a distal end with a strap interface for attaching to the patient transport apparatus, and a proximal end; and a guard configured for removable attachment to the proximal end of the strap, the guard including: a base defining a channel arranged to receive the proximal end of the strap therein; a keeper arranged for movement relative to the base between: a released position to permit movement of the proximal end of the strap along the channel of the base, and a secured position to restrict movement of the proximal end of the strap out of the channel; and a retainer coupled between the base and the keeper and being operable between: an engaged configuration to retain the keeper in the secured position, and a disengaged configuration to permit movement of the keeper between the secured position and the released position.

A patient support system is provided. The patient support system comprises: a patient transport apparatus; a harness assembly comprising: a strap for securing a patient to the patient transport apparatus, the strap defining a distal end with a strap interface for attaching to the patient transport apparatus, and a proximal end; and a guard configured for removable attachment to the proximal end of the strap, the guard including: a base defining a channel arranged to receive the proximal end of the strap therein; a keeper arranged for movement relative to the base between: a released position to permit movement of the proximal end of the strap along the channel of the base, and a secured position to restrict movement of the proximal end of the strap out of the channel; and a retainer coupled between the base and the keeper and being operable between: an engaged configuration to retain the keeper in the secured position, and a disengaged configuration to permit movement of the keeper between the secured position and the released position.

BRIEF DESCRIPTION OF THE DRAWINGS

Other advantages of the present invention will be readily appreciated as the same becomes better understood by reference to the following detailed description when considered in connection with the accompanying drawings.

DETAILED DESCRIPTION OF THE VERSIONS

Figure 1:
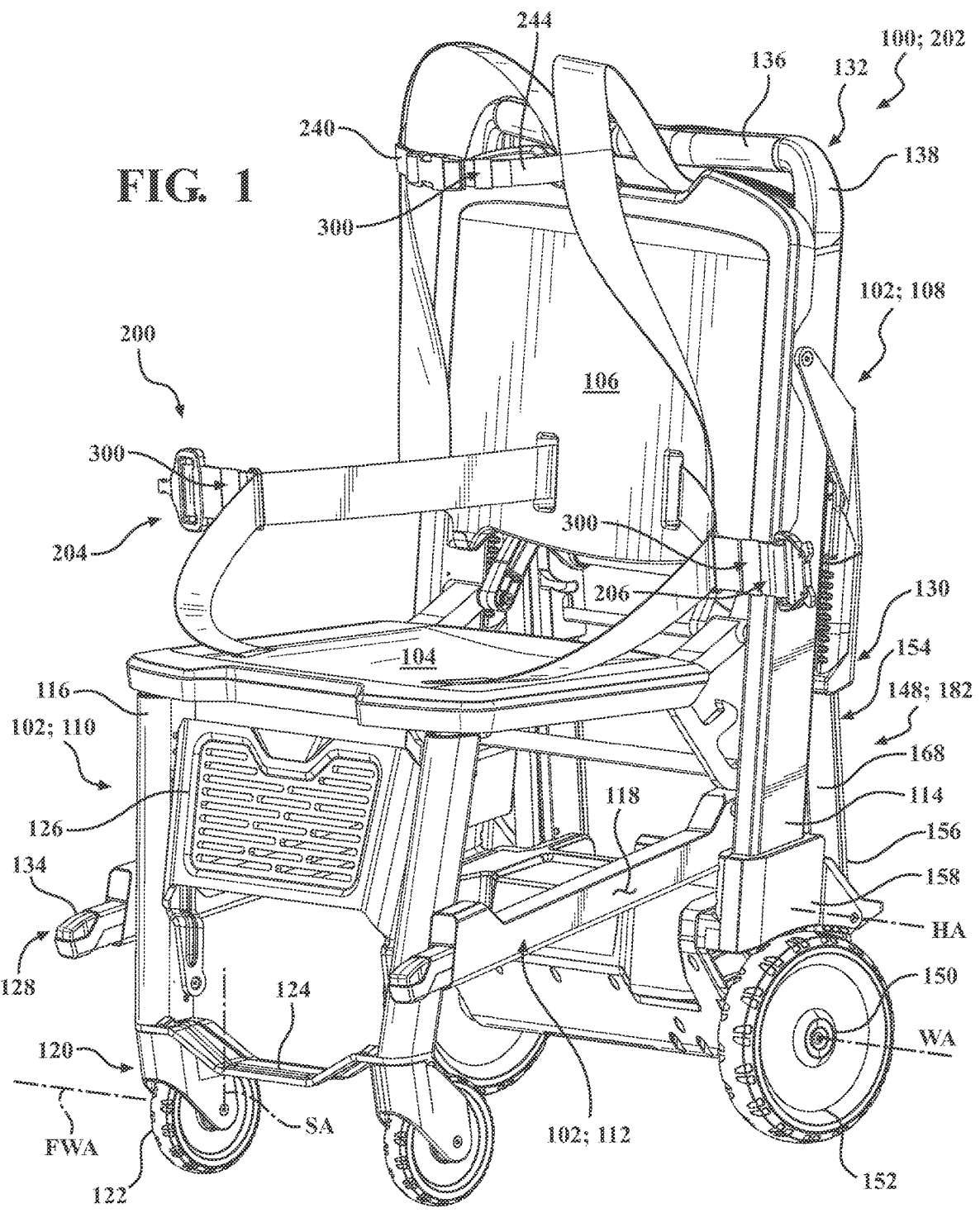
FIG. 1 is a front perspective view of a patient transport apparatus and a front perspective view of a patient support system according to the present disclosure.

Referring now to the drawings, wherein like numerals indicate like parts throughout the several views, the present disclosure is generally directed toward the use of one or more types of patient transport apparatus 100 configured to allow one or more caregivers to transport a patient. The representative patient transport apparatus 100 illustrated throughout the drawings is realized as a "stair chair" which can be operated in a chair configuration to transport the patient across ground or floor surfaces (e.g., pavement, hallways, and the like) and/or during ingress into or egress out of a structure (e.g., a home or building) as shown in FIG. 1, as well as in a stair configuration and/or a stowed configuration (not shown in detail herein). In some versions, the patient transport apparatus 100 may be similar to as is disclosed in U.S. Patent Application Publication No. 2021/0196535, entitled "Patient Containment Systems For Use With Patient Transport Apparatuses," the disclosure of which is hereby incorporated by reference in its entirety. While the representative patient transport apparatus 100 illustrated and described herein is realized as a stair chair, those having ordinary skill in the art will appreciate that aspects of the present disclosure could be utilized with any suitable type, style, and/or configurations of patient transport apparatus 100. By way of non-limiting example, the patient transport apparatus 100 could be realized as a cot, a stretcher, a backboard, a hospital bed, a wheelchair, and the like. Other configurations are contemplated.

As is best shown in FIG. 1, the illustrated patient transport apparatus 100 comprises a support structure 102 to which a seat section 104 and a back section 106 are operatively attached. The seat section 104 and the back section 106 are each shaped and arranged to provide support to the patient during transport. The support structure 102 generally includes a rear support assembly 108, a front support assembly 110, and an intermediate support assembly 112. The back section 106 is coupled to the rear support assembly 108 for concurrent movement. To this end, the rear support assembly 108 comprises rear uprights 114 which extend generally vertically and are secured to the back section 106, such as with fasteners (not shown in detail). The rear uprights 114 are spaced generally laterally from each other in the illustrated versions and are formed from separate components which cooperate to generally define the rear support assembly 108. However, those having ordinary skill in the art will appreciate that other configurations are contemplated, and the rear support assembly 108 could comprise or otherwise be defined by any suitable number of components. The front support assembly 110 comprises front struts 116 which, like the rear uprights 114, are spaced laterally from each other and extend generally vertically. The intermediate support assembly 112 comprises intermediate arms 118 which are also spaced laterally from each other. Here, too, it will be appreciated that other configurations are contemplated, and the front support assembly 110 and/or the intermediate support assembly 112 could comprise or otherwise be defined by any suitable number of components.

In some instances, the intermediate support assembly 112 and the seat section 104 each may be pivotably coupled to the rear support assembly 108. Additionally, the intermediate support assembly 112 and the seat section 104 each may be pivotably coupled to the front support assembly 110, such as is disclosed in U.S. Patent Application Publication No. 2021/0196535, previously referenced. Furthermore, for each of the pivotable connections disclosed herein, it will be appreciated that one or more fasteners, bushings, bearings, washers, spacers, and the like may be provided to facilitate smooth pivoting motion between various components.

Referring to FIG. 1, the front support assembly 110 includes a pair of caster assemblies 120, each of which comprises a front wheel 122 arranged to rotate about a respective front wheel axis FWA and to pivot about a respective swivel axis SA (axes not shown in detail). The caster assemblies 120 are generally arranged on opposing lateral sides of the front support assembly 110 and are operatively attached to the front struts 116. A lateral brace 124 extends laterally between the front struts 116 to, among other things, afford rigidity to the support structure 102. Here, a foot rest 126 is pivotably coupled to each of the front struts 116 adjacent to the caster assemblies 120 to provide support to the patient's feet during transport.

The representative versions of the patient transport apparatus 100 illustrated throughout the drawings comprise different handles arranged for engagement by caregivers during patient transport. More specifically, the patient transport apparatus 100 comprises front handle assemblies 128, pivoting handle assemblies 130, and an upper handle assembly 132 (hereinafter referred to as "handle assembly 132"), as described in greater detail below. A stowed position and an engagement position of the pivoting handle assemblies 130 and the handle assembly 132 are further described and shown in U.S. Patent Application Publication No. 2021/0196535, previously referenced.

The front handle assemblies 128 are configured to be operated in a collapsed position and an extended position (not shown). The front handle assemblies 128 are shown in the collapsed position in FIG. 1. The front handle assemblies 128 may be slidably supported by bushings, bearings, and the like coupled to the intermediate arms 118, and may be lockable in and/or between the collapsed position and the extended position via respective front handle locks 134 shown in FIG. 1. A caregiver may engage the front handle locks 134 (not shown in detail) to facilitate moving the front handle assemblies 128 between the collapsed position and the extended position. The front handle assemblies 128 are generally arranged so as to be engaged by a caregiver during patient transport up or down stairs when in the extended position. It will be appreciated that the front handle assemblies 128 could be of various types, styles, and/or configurations suitable to be engaged by caregivers to support the patient transport apparatus 100 for movement. While the illustrated front handle assemblies 128 are arranged for telescoping movement, other configurations are contemplated. By way of non-limiting example, the front handle assemblies 128 could be pivotably coupled to the support structure 102 or other parts of the patient transport apparatus 100. In some versions, the front handle assemblies 128 could be configured in a manner similar to that disclosed in U.S.

Pat. No. 6,648,343, the disclosure of which is hereby incorporated by reference in its entirety.

The pivoting handle assemblies 130 are configured to be operated in a stowed position and an engagement position (not shown). The pivoting handle assemblies 130 are shown in the stowed position in FIG. 1. The pivoting handle assemblies 130 are coupled to the respective rear uprights 114 of the rear support assembly 108, and are movable relative to the rear uprights 114 between the stowed position and the engagement position. Like the front handle assemblies 128, the pivoting handle assemblies 130 are generally arranged for engagement by a caregiver during patient transport, and may advantageously be utilized in the engagement position when the patient transport apparatus 100 operates in the chair configuration to transport the patient across floor surfaces. In some versions, the pivoting handle assemblies 130 could be configured in a manner similar to that disclosed in U.S. Pat. No. 6,648,343, previously referenced. Other configurations are contemplated.

Figure 3:
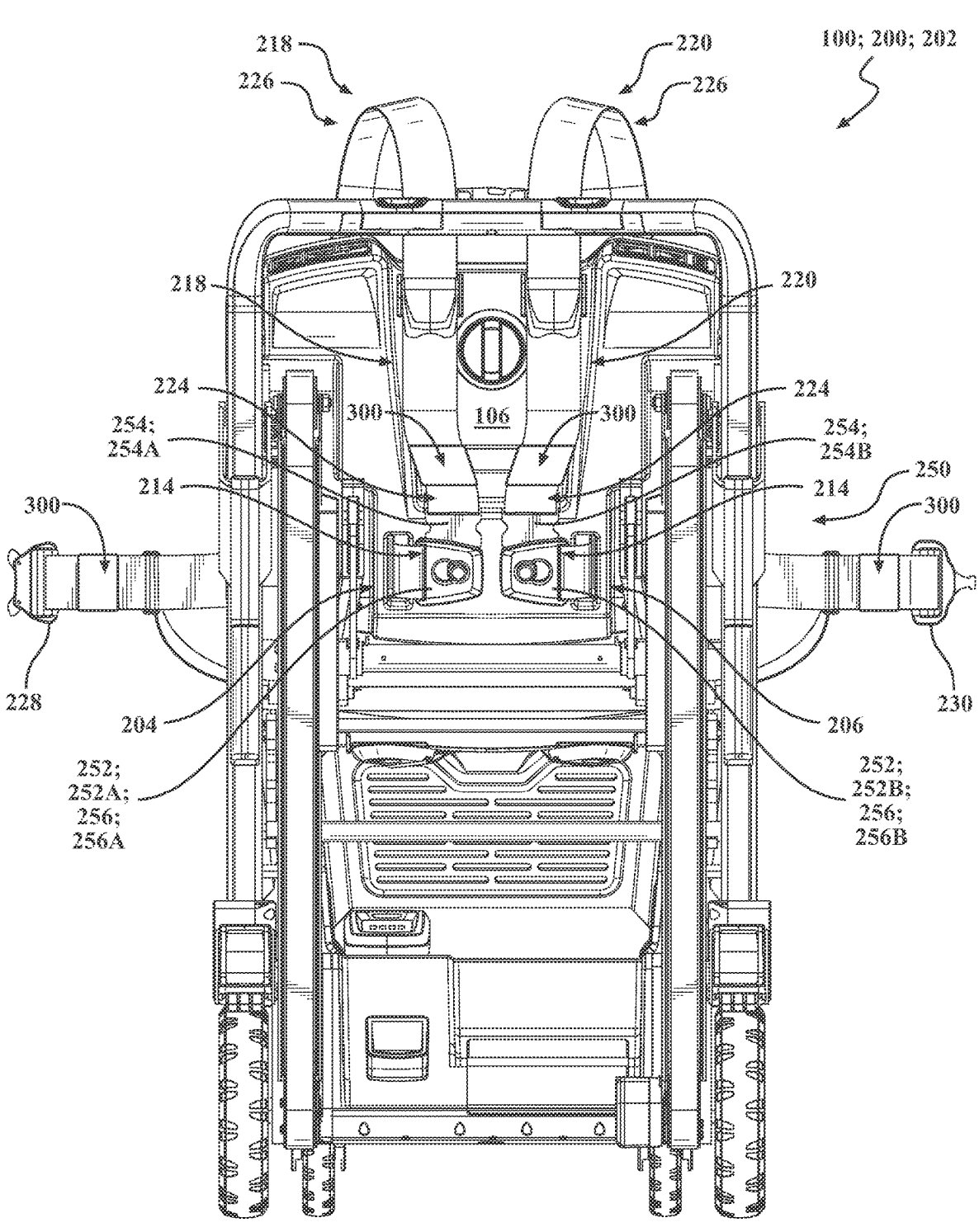
FIG. 3 is a rear perspective view of the patient transport apparatus of FIGS. 1-2 and a rear perspective view of the patient support system in FIGS. 1-2.

The handle assembly 132 is configured to be operated in a collapsed position and an extended position (not shown). The handle assembly 132 is shown in the collapsed position in FIG. 1. The handle assembly 132 is also coupled to the rear support assembly 108, and generally comprises an upper grip 136 operatively attached to extension posts 138 which are supported within the respective rear uprights 114 for movement between the collapsed position and the extended position 132B. To this end, the extension posts 138 of the handle assembly 132 may be slidably supported by bushings, bearings, and the like coupled to the rear uprights 114, and may be lockable in and/or between the collapsed position and the extended position via an extension lock mechanism with an extension lock release arranged for engagement by the caregiver (not shown in detail). As is best shown in FIG. 3, the extension lock release 142 may be realized as a rotatable knob in communication with a flexible cable (not shown) which extends generally laterally between the rear uprights 114 and supports a cable connected to extension lock mechanisms 140 (not shown in detail) which releasably engage the extension posts 138 to maintain the handle assembly 132 between the extended position and the collapsed position. Here, it will be appreciated that the extension lock mechanism 140 and/or the extension lock release 142 could be of a number of different styles, types, configurations, and the like sufficient to facilitate selectively locking the handle assembly 132 in the extended position. In some versions, the handle assembly 132, the extension lock mechanism 140, and/or the extension lock release 142 could be configured in a manner similar to that disclosed in U.S. Pat. No. 6,648,343, previously referenced. Other configurations are contemplated.

The illustrated patient transport apparatus 100 includes elements for transitioning between the chair configuration and the stair configuration. For example, in the representative version illustrated herein, the patient transport apparatus 100 includes a carrier assembly 148 arranged for movement relative to the support structure 102 between the chair configuration and the stair configuration. The carrier assembly 148 generally comprises at least one shaft 150 defining a wheel axis WA, one or more rear wheels 152 supported for rotation about the wheel axis WA, at least one track assembly 154 having a belt 156 for engaging stairs ST, and one or more hubs 158 supporting the shaft 150 and the track assembly 154 for concurrent pivoting movement about a hub axis HA. Here, movement of the carrier assembly 148 from the chair configuration to the stair configuration simultaneously deploys the track assembly 154 for engaging stairs with the belt 156 and moves the wheel axis WA longitudinally closer to the front support assembly 110 so as to position the rear wheels 152 further underneath the seat section 104 and closer to the front wheels 122. Operation along stairs ST is disclosed in U.S. Patent Application Publication No. 2021/0196535, previously referenced.

The illustrated patient transport apparatus 100 includes elements for aiding the transport of a patient across a floor surface and up and down stairs. For example, in the representative version illustrated herein, the track assemblies 154 each comprise a rail 168, the belt 156 of the track assemblies 154 being arranged for movement relative to the rail 168 to facilitate movement of the patient transport apparatus 100 up and down stairs. The patient transport apparatus 100 also comprises a drive system, generally indicated at 182, configured to facilitate driving the belts 156 of the track assemblies 154 relative to the rails 168 to facilitate movement of the patient transport apparatus 100 up and down stairs. The patient transport apparatus 100 comprises a control system and a user interface (not shown in detail) to, among other things, facilitate control of the track assemblies 154.

Referring to FIG. 1, a harness assembly 200 to secure the patient to the patient transport apparatus 100 is generally shown. The harness assembly 200 may be removably engaged, coupled, or otherwise attached to the patient transport apparatus 100 to define a patient support system 202 according to the present disclosure. FIGS. 1-4 depict the patient support system 202 with the harness assembly 200 engaged with the patient transport apparatus 100. The harness assembly 200 may function to retain a patient supported for transport on the patient transport apparatus 100, particularly during transport along a floor surface, during ingress into or egress out of a structure (e.g., a home or building), and/or during transport up or down stairs.

Figure 2:
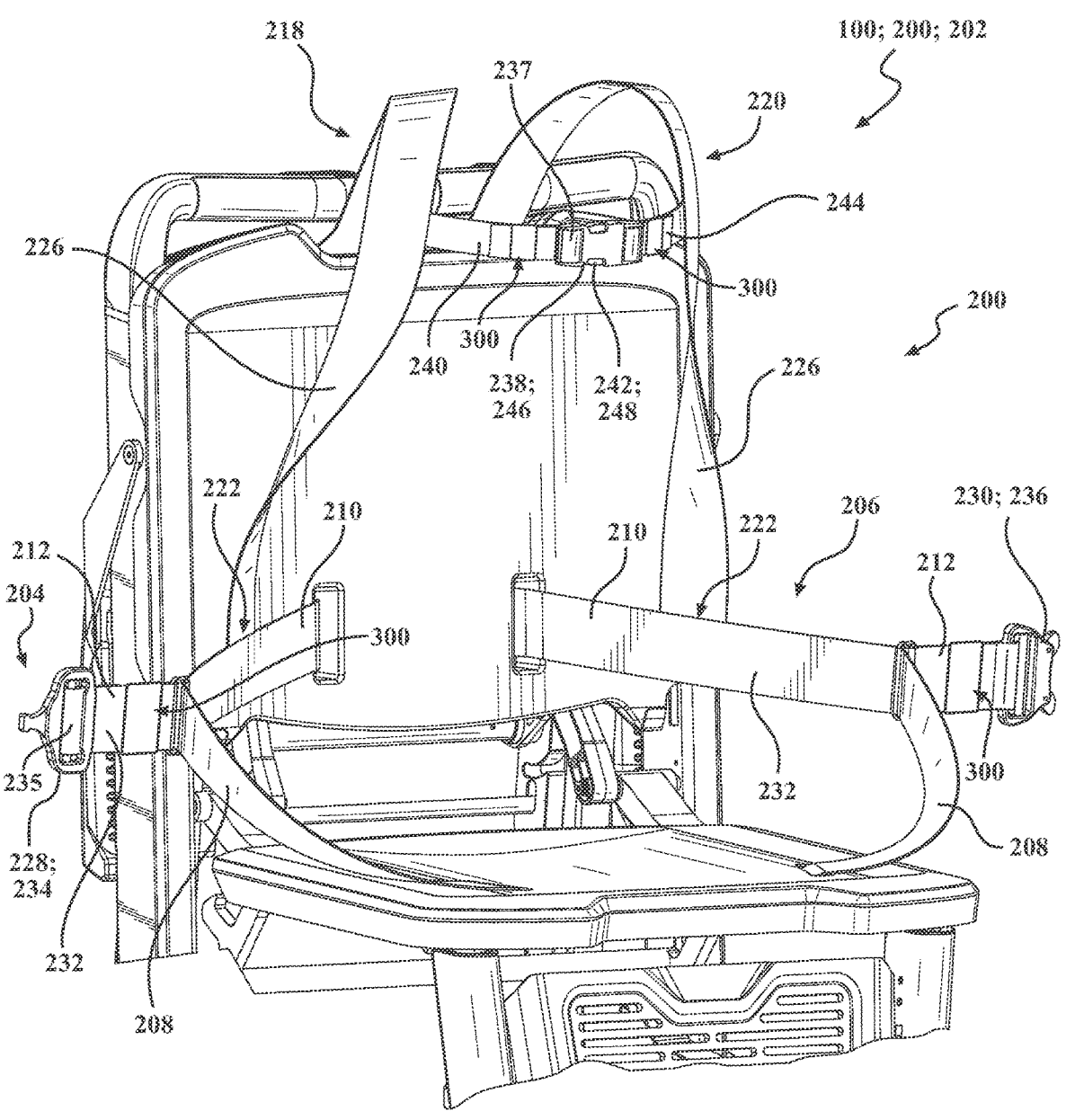
FIG. 2 is a partial view of the patient transport apparatus of FIG. 1 and a perspective view of the patient support system in FIG. 1.

The harness assembly 200 is designed to secure patients of various sizes through the use of straps which are removably attachable to the patient transport apparatus 100. To this end, and as is best depicted in FIG. 2, in some versions, the harness assembly 200 may comprise a first lower strap 204 and a second lower strap 206, each having a respective thigh region 208, waist region 210, and connection region 212 arranged between a back end 214 (shown in FIG. 3) and a seat end 216 (shown in FIG. 4). The connection region 212 is arranged between the thigh region 208 and the waist region 210, the thigh region 208 is arranged between the connection region 212 and the seat end 216, and the waist region 210 is arranged between the connection region 212 and the back end 214.

It will be appreciated that the thigh regions 208, the waist regions 210, and the connection regions 212 could be formed or otherwise defined in a number of different ways. By way of non-limiting example, the first and second lower straps 204, 206 could each be formed as unitary, one piece components between the back end 214 and the seat end 216, which taper or otherwise transition between the thigh region 208, the connection region 212, and the waist region 210. It is also contemplated that the first and second lower straps 204, 206 could be respectively formed from multiple components that are secured together (e.g., welded, bonded, adhered, and the like) and cooperate to define the thigh region 208, the connection region 212, and the waist region 210. By way of non-limiting example, a strap could extend between the back end 214 and the seat end 216, and separate components that are secured to the strap could define the thigh region 208 and/or the waist region 210 (not shown). Other configurations are contemplated. In some versions one or more portions of the harness assembly 200 may comprise polymeric material, such as polyurethane, or other suitable materials to ease cleaning, and may comprise multiple materials (e.g., coated fabric). The components of the harness assembly 200 may provide a smooth, continuous, outer surface for wiping and thereby cleaning, and may be waterproof, water-resistant, and/or impervious to contaminants, such as dirt, grease, and body fluids. Other configurations are contemplated.

Referring to FIG. 2, in some versions, the harness assembly 200 may comprise a first upper strap 218 and a second upper strap 220 each having a respective front end 222, back end 224 (see FIG. 3), and shoulder region 226 extending between the front end 222 and the back end 224. As shown in FIG. 1, the front end 222 of the first upper strap 218 and the front end 222 of the second upper strap 220 are coupled to the respective lower strap 204, 206. The straps of the harness assembly 200 may be attached to the patient transport apparatus 100 using a strap interface (not shown in detail) realized by various arrangements of connectors, coupling brackets, latches, loops, and the like configured to releasably secure to the patient transport apparatus 100.

Referring to FIG. 2, in the illustrated version, a first connector 228 is coupled to the connection region 212 of the first lower strap 204, and a second connector 230 is coupled to the connection region 212 of the second lower strap 206. The first and second connectors 228, 230 may be coupled to the connection regions 212 via a guide 232, the guide 232 being configured to slide between the seat end 216 and the back end 214. The connectors 228, 230 cooperate to facilitate releasably attaching the first lower strap 204 and second lower strap 206 together to at least partially limit movement of the first lower strap 204 relative to the second lower strap 206 (and/or relative to each other). In the representative version illustrated herein, one of the first and second connectors 228, 230 is realized as a lower clasp 234, and the other of the first and second connectors 228, 230 is realized as a lower buckle 236 configured to releasably secure to the lower clasp 234. However, it will be appreciated that the first and second connectors 228, 230 could be configured in a number of different ways sufficient to limit movement between the first and second lower straps 204, 206.

Also shown in FIG. 2, in some versions, a first shoulder connector 238 is coupled to the shoulder region 226 of the first upper strap 218 via an extension strap 240, and a second shoulder connector 242 is coupled to the shoulder region 226 of the second upper strap 220 via another extension strap 244. The second shoulder connector 242 is configured to releasably attach to the first shoulder connector 238 to at least partially limit movement of the first upper strap 218 relative to the second upper strap 220 (and/or relative to each other). In the representative version illustrated herein, one of the first and second shoulder connectors 238, 242 is realized as an upper clasp 246, and the other of the first and second shoulder connectors 238, 242 is realized as an upper buckle 248 configured to releasably secure to the upper clasp 246. However, it will be appreciated that the first and second shoulder connectors 238, 242 could be configured in a number of different ways sufficient to limit movement between the first and second upper straps 218, 220.

Figure 4:
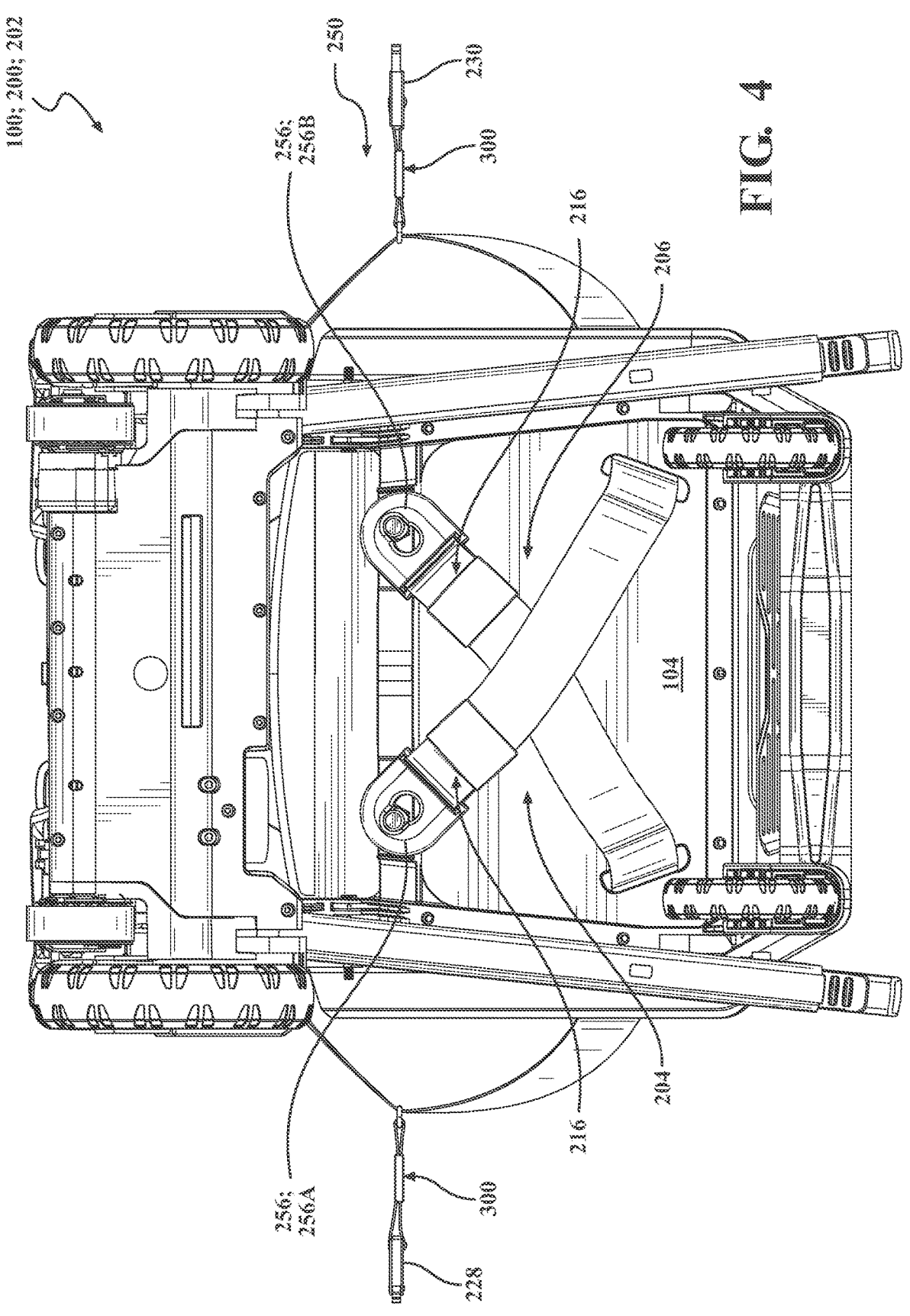
FIG. 4 is a bottom perspective view of the patient transport apparatus of FIGS. 1-3 and a rear perspective view of the patient support system in FIGS. 1-3.

Referring now to FIGS. 3 and 4, in the representative version illustrated herein, the patient support system 202 comprises a coupling system 250 to facilitate releasable attachment of portions of the harness assembly 200 to portions of the patient transport apparatus 100. Referring to FIG. 3, the coupling system 250 may include a back section coupling bracket 252 coupled to the back end 214 of a lower strap 204, 206, the back section coupling bracket 252 configured for removable attachment to the back section 106 of the patient transport apparatus 100. The coupling system 250 also includes a latch 254 coupled to the back end 224 of an upper strap 218, 220. The back section coupling bracket 252 may be configured to removably receive the latch 254 to retain the upper strap 218, 220 coupled to the latch 254 together with the latch 254 relative to the coupling bracket 252. Referring to FIG. 4, the coupling system 250 may also include a seat section coupling bracket 256 coupled to the seat end 216 of a lower strap 204, 206, the seat section coupling bracket 256 configured for removable attachment to the seat section 104 of the patient transport apparatus 100. In the representative version shown in FIG. 2, the coupling system 250 includes first back section coupling bracket 252A, a second back section coupling bracket 252B, a first latch 254A and a second latch 254B, a first seat section coupling bracket 256A, and a second seat section coupling bracket 256B. It should be noted that a shape and/or structure of the back section coupling bracket 252, the latch 254, and the seat section coupling bracket 256, and any other components of the coupling system 250 may vary and may be configured in other ways.

Referring to FIGS. 1-4, the harness assembly 200 may include a strap management guard 300 removably attached to a strap of the harness assembly 200. The strap management guard 300 provides several advantages to the patient support system 202. For example, the strap management guard 300 is configured to help caregivers efficiently manage an excess length of a strap, as is described in greater detail below. As another advantage, the strap management guard 300 may protect an end of a strap by preventing fraying at the end of the strap. As yet another advantage, the strap management guard may prevent a strap from decoupling from a connector, coupling bracket, or latch. For example, referring to FIG. 2, the strap management guard 300 coupled to the first lower strap 204 may prevent the first lower strap 204 from decoupling from the first connector 228. Specifically, the strap management guard 300 may be sized to prevent the strap management guard 300 and the portion of the first lower strap 204 to which the strap management guard 300 is removably attached from passing through a void 235 of the lower clasp 234. As another example, the strap management guard 300 may be sized to prevent the strap management guard 300 and the portion of the extension strap 240 to which the strap management guard 300 is removably attached from passing through a void 237 of the first shoulder connector 238.

The harness assembly 200 may include any suitable number of strap management guards 300. For instance, the harness assembly 200 may include a strap management guard 300 removably attached to one or more of the extension strap 240, the extension strap 244, the first upper strap 218, the second upper strap 220, the first lower strap 204, and/or the second lower strap 206. As shown in FIG. 2, a strap management guard 300 is removably attached to the first lower strap 204, a second strap management guard 300 is removably attached to the second lower strap 206, a third strap management guard 300 is removably attached to the extension strap 240, and a fourth strap management guard 300 is removably attached to the extension strap 244. As another example shown in FIG. 3, a fifth strap management guard 300 is removably attached to a back end 224 of the first upper strap 218 and a sixth strap management guard 300 is removably attached to a back end 224 the second upper strap 220.

The strap management guard 300 and components thereof (to be described herein) may be formed of any suitable material. For example, the strap management guard 300 may be formed of a metal (such as aluminum) or metal alloy (such as an aluminum alloy) and/or a polymeric material and/or an elastomeric material. Furthermore, it should be noted that the strap management guard 300 and components thereof may include any structure, shape, and size suitable for proper operation of the strap management guard 300, as described herein.

Figure 5:
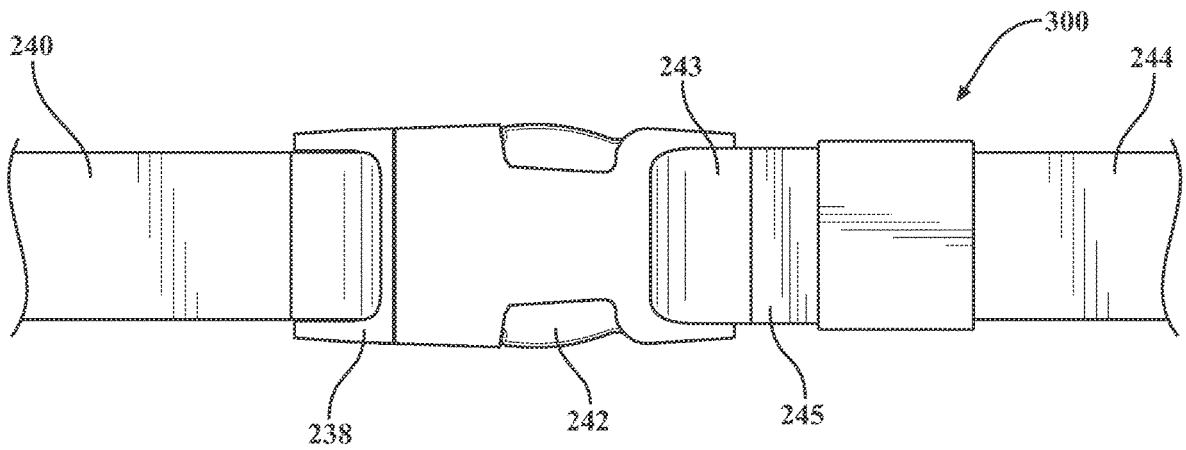
FIG. 5 is a perspective view of a first shoulder connector, a second shoulder connector, and a strap management guard of the patient support system in FIGS. 1-4.

FIG. 5 illustrates a strap management guard 300 removably attached to a proximal end 245 of the extension strap 244 and the distal end 243 of the extension strap 244 is coupled to the second shoulder connector 242. Generally, the strap management guard 300 is removably attached to a proximal end of a strap (any strap described herein), whereas the distal end of the strap is coupled to a strap interface (e.g. any connector, coupling bracket, or latch described herein). In this way, the strap management guard 300 may be attached to a strap and, by being coupled to a strap interface, the strap may be attached to the patient transport apparatus 100.

Herein, a proximal end of a strap may refer to a proximal end of any portion of any strap. Furthermore, a distal end of a strap may refer to a distal end of any portion of any strap. Furthermore, a single strap may include more than one proximal and distal end. In this way, more than one strap management guard 300 may be removably attached to a single strap. For example, referring to FIGS. 2 and 4, a strap management guard 300 may be removably attached to a proximal end of the second lower strap 206 (resulting in placement proximate the second connector 230, which is coupled to a distal end of the second lower strap 206) and to a proximal end of the seat end 216 of the second lower strap 206 (resulting in placement proximate the first seat section coupling bracket 256A, which is coupled to a distal end of the seat end 216 of the second lower strap 206). Additionally, in an unshown instance, a strap management guard 300 may also be removably attached to a proximal end of the back end 214 of the second lower strap 206 (resulting in placement proximate the second back section coupling bracket 252B, which is coupled to a distal end of the back end 214 of the second lower strap 206)

Figure 6:
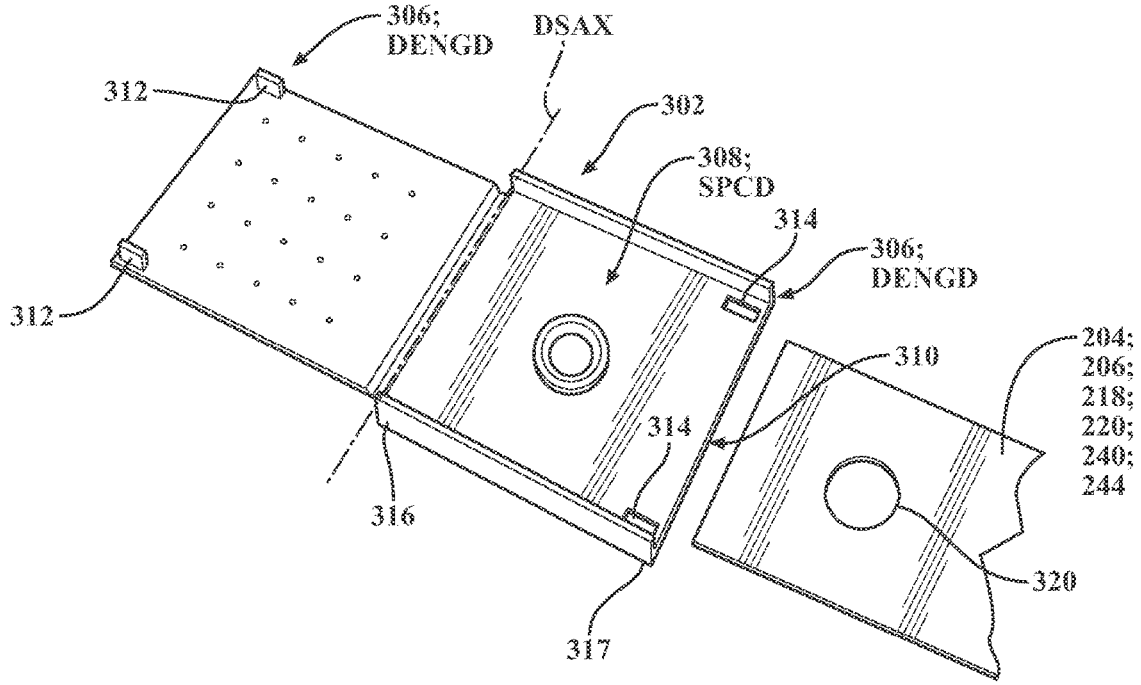
FIG. 6 is a perspective view of a first instance of the strap management guard of the patient support system in FIGS. 1-4.
Figures 7A, 7B, 7C:
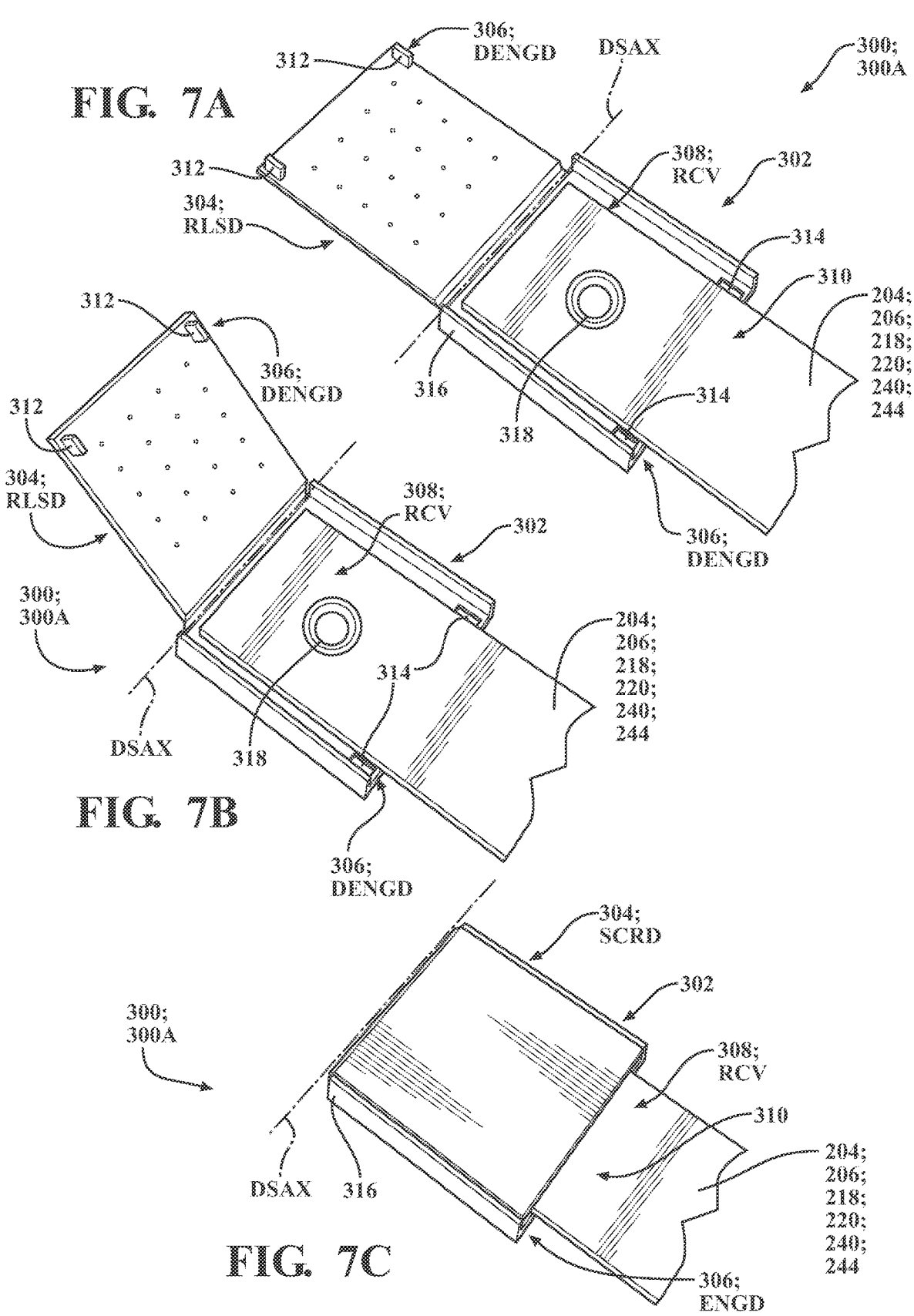
FIGS. 7A-7C are perspective views illustrating an operation of the strap management guard of FIG. 6.
Figure 8:
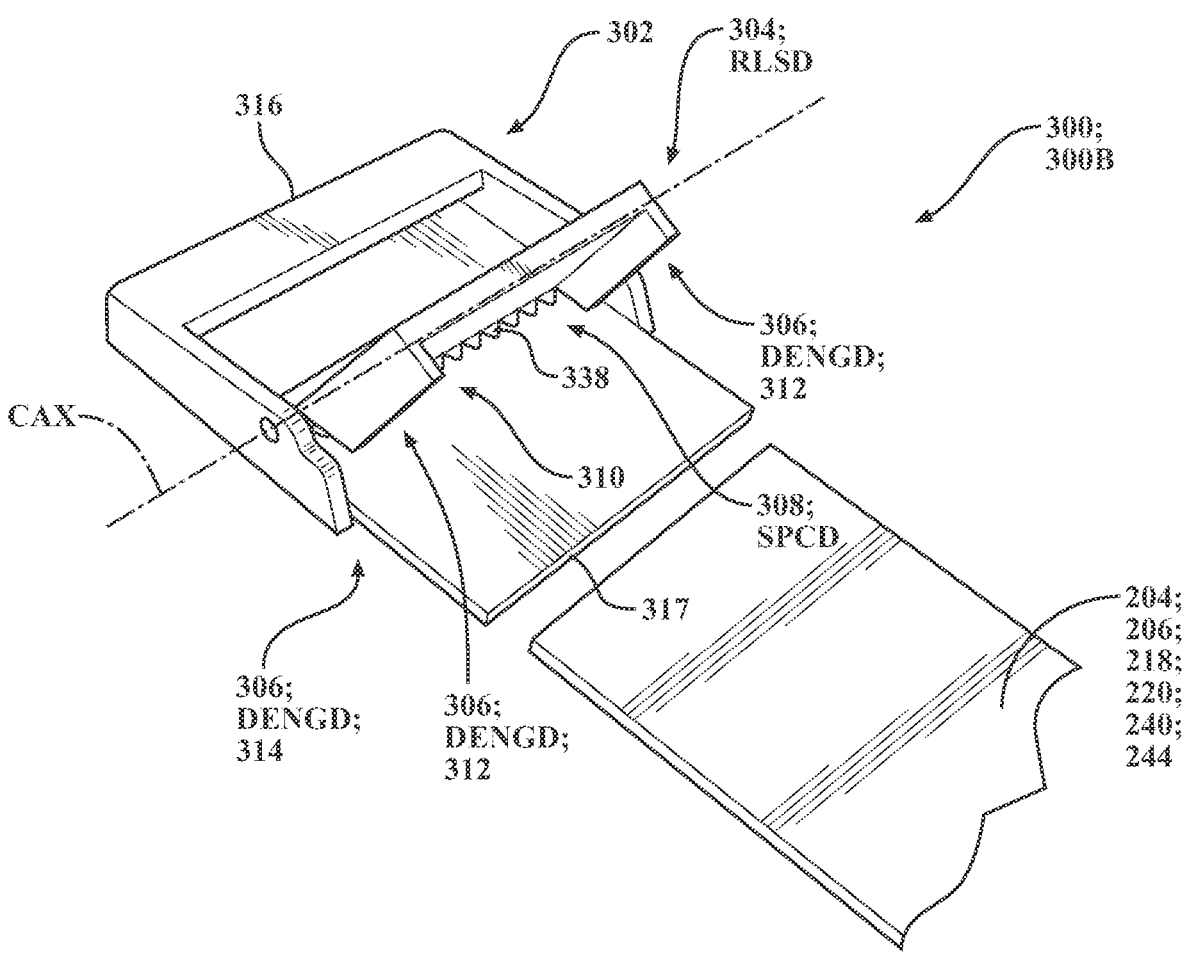
FIG. 8 is a perspective view of a second instance of the strap management guard of the patient support system in FIGS. 1-4.

Three instances of the strap management guard 300 are shown in FIGS. 6-11C. The instance of the strap management guard 300 shown in FIGS. 6 and 7A-7C is referred to herein as the "door strap management guard 300A". The instance of the strap management guard 300 shown in FIGS. 8 and 9A-9B is referred to herein as the "cam strap management guard 300B". The instance of the strap management guard 300 shown in FIGS. 10A-10C and 11A-11C is referred to herein as the "slider strap management guard 300C".

Although the strap management guards 300 shown in FIGS. 6-11C vary structurally, each of the strap management guards 300 includes components that perform common functions. For example, each strap management guard 300A, 300B, 300C includes a base 302, a keeper 304, and a retainer 306. The base 302 defines a channel 308. The channel 308 defines an inlet 310. The retainer 306 is coupled between the base 302 and the keeper 304. The retainer 306 includes a protrusion 312 coupled to the keeper 304. The retainer 306 also includes a receiver 314 formed in the base 302 shaped to receive the protrusion 312.

The channel 308 of the strap management guard 300 may be arranged to receive the proximal end of the strap therein. Furthermore, the channel 308 of the strap management guard 300 may be arranged to receive the proximal end of any strap described herein. As noted in FIGS. 6-11C, the strap may be any one of the extension strap 240, the extension strap 244, the first upper strap 218, the second upper strap 220, the first lower strap 204, and the second lower strap 206 of the harness assembly 200.

The channel 308 is operable between a received configuration RCV and a spaced configuration SPCD. In the received configuration RCV, the channel 308 receives a proximal end of the strap 204, 206, 218, 220, 240, 244 therein via the inlet 310. In the spaced configuration SPCD, the channel 308 is spaced from the strap 204, 206, 218, 220, 240, 244 such that the channel 308 does not receive a proximal end of the strap 204, 206, 218, 220, 240, 244.

Figures 9A, 9B:
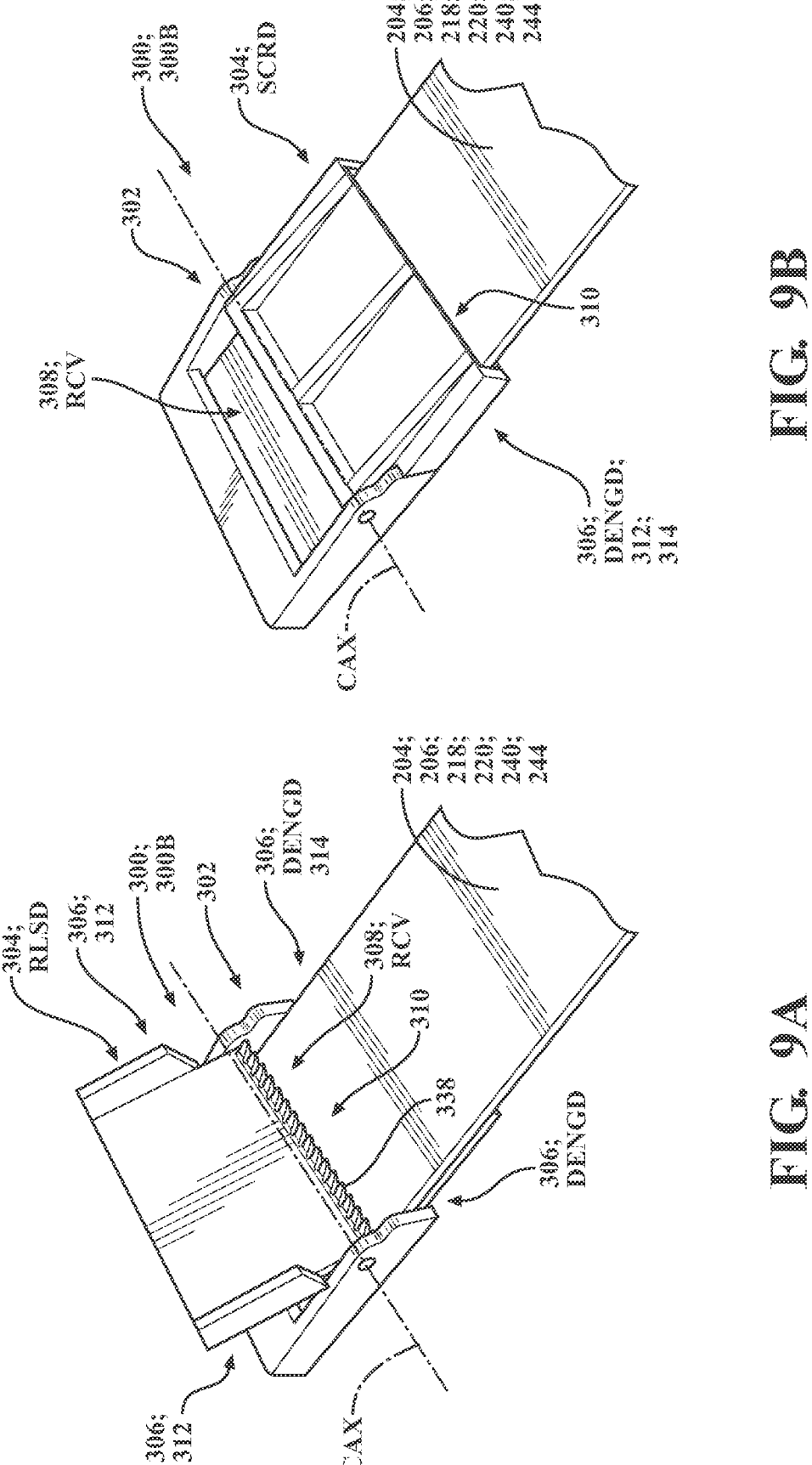
FIGS. 9A-9B are perspective views illustrating an operation of the strap management guard of FIG. 8.
Figure 10A:
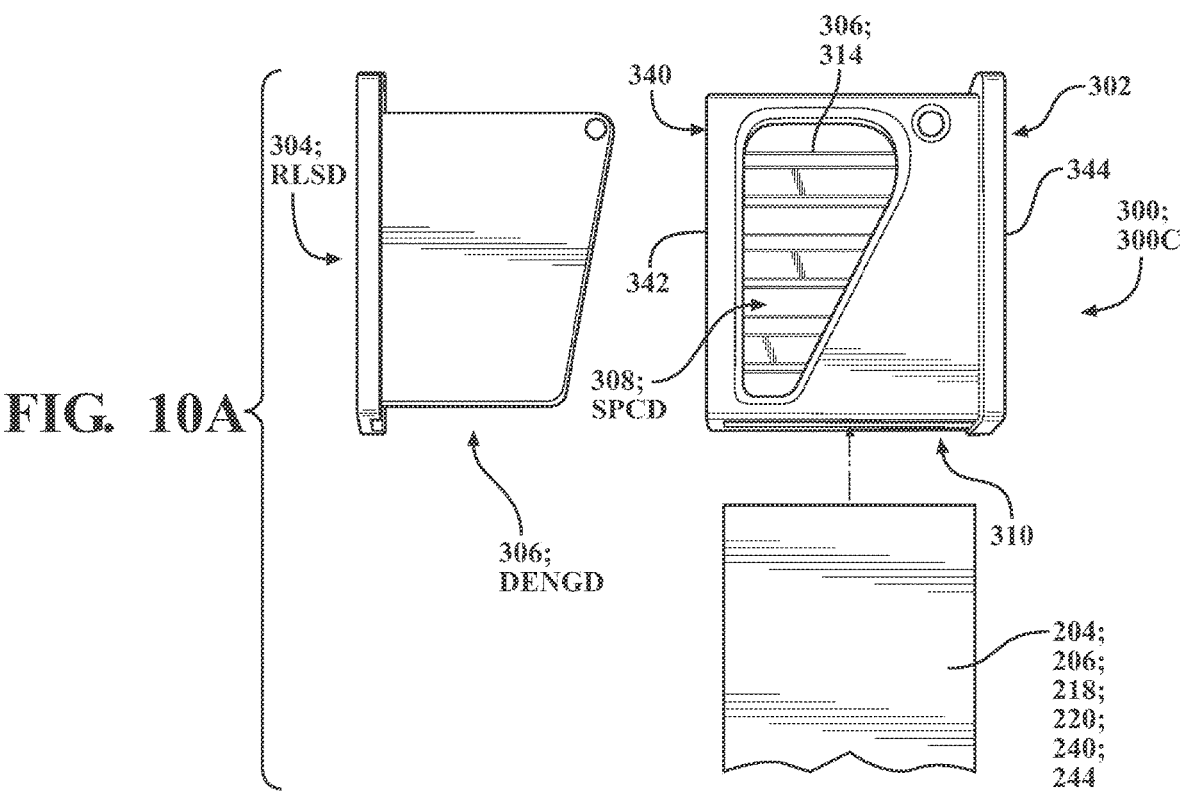
FIGS. 10A-10B are perspective view of a third instance of the strap management guard of the patient support system in FIGS. 1-4.
Figure 10B:
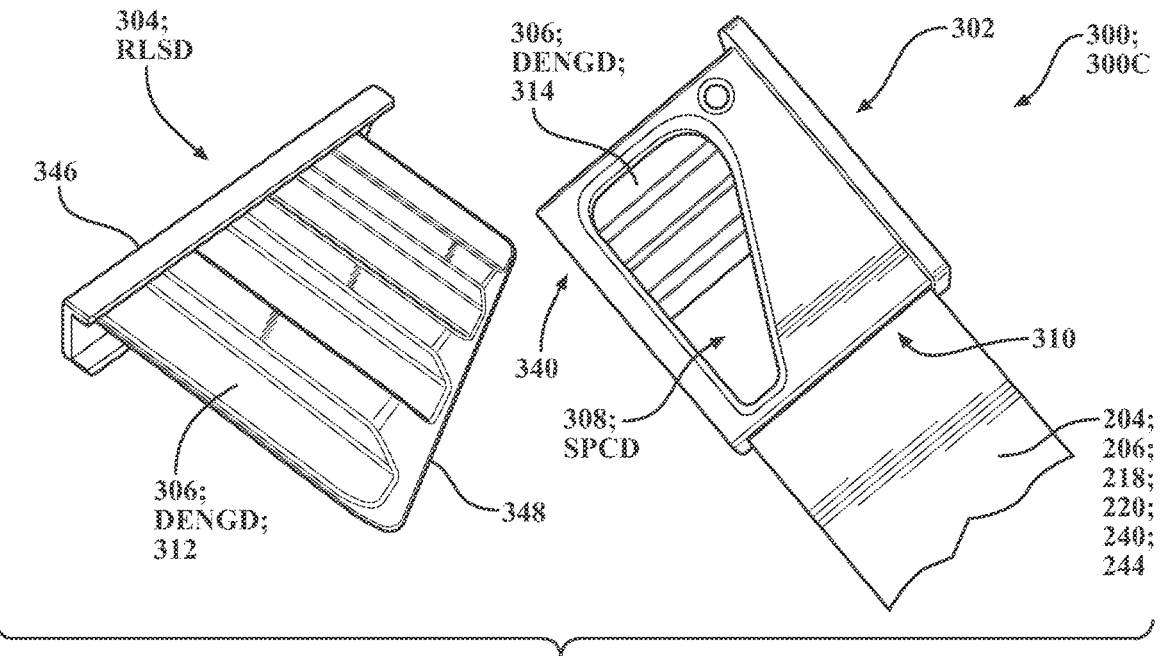

The received configuration RCV of the channel 308 of the door strap management guard 300A is shown in FIGS. 7A-7C and the spaced configuration SPCD of the channel 308 of the door strap management guard 300A is shown in FIG. 6. The received configuration RCV of the channel 308 of the cam strap management guard 300B is shown in FIGS. 9A-9B and the spaced configuration SPCD of the channel 308 of the cam strap management guard 300B is shown in FIG. 8. The received configuration RCV of the channel 308 of the slider strap management guard 300C is shown in FIGS. 10C and 11A-11C and the spaced configuration SPCD of the channel 308 of the slider strap management guard 300C is shown in FIGS. 10A-10B.

The keeper 304 is arranged for movement relative to the base 302 between a released position RLSD and a secured position SCRD. In the released position RLSD, the keeper 304 permits movement of the proximal end of the strap 204, 206, 218, 220, 240, 244 along the channel 308 of the base 302. In the secured position SCRD, the keeper 304 restricts movement of the proximal end of the strap 204, 206, 218, 220, 240, 244 out of the channel 308 of the base 302. In other words, in the released position RLSD, a user of the strap management guard 300 may remove the strap 204, 206, 218, 220, 240, 244 from the channel 308. In the secured position SCRD, a user of the strap management guard 300 is inhibited from removing the strap 204, 206, 218, 220, 240, 244 from the channel 308.

Figure 10C:
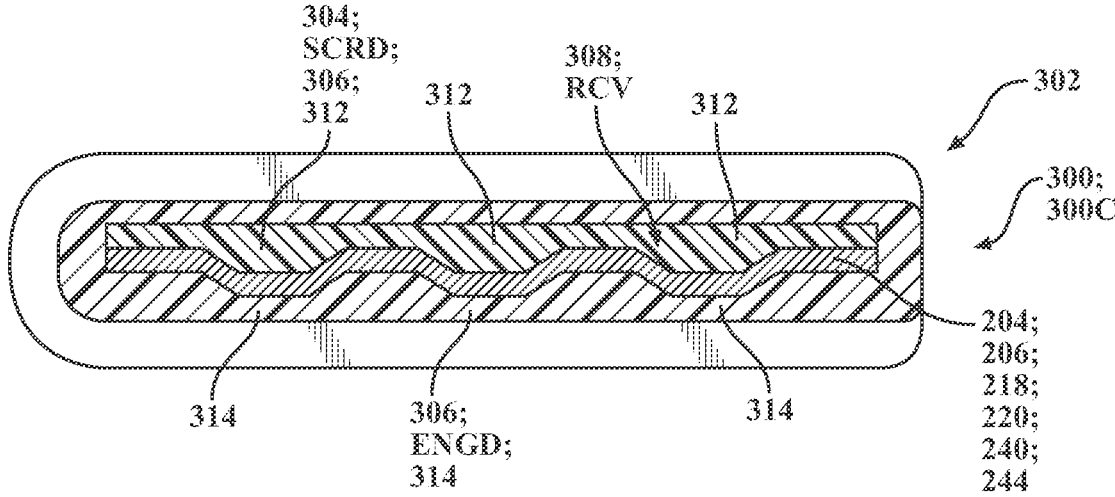
FIG. 10C is a cutaway view of the strap management guard of FIGS. 10A and 10B.
Figure 11A:
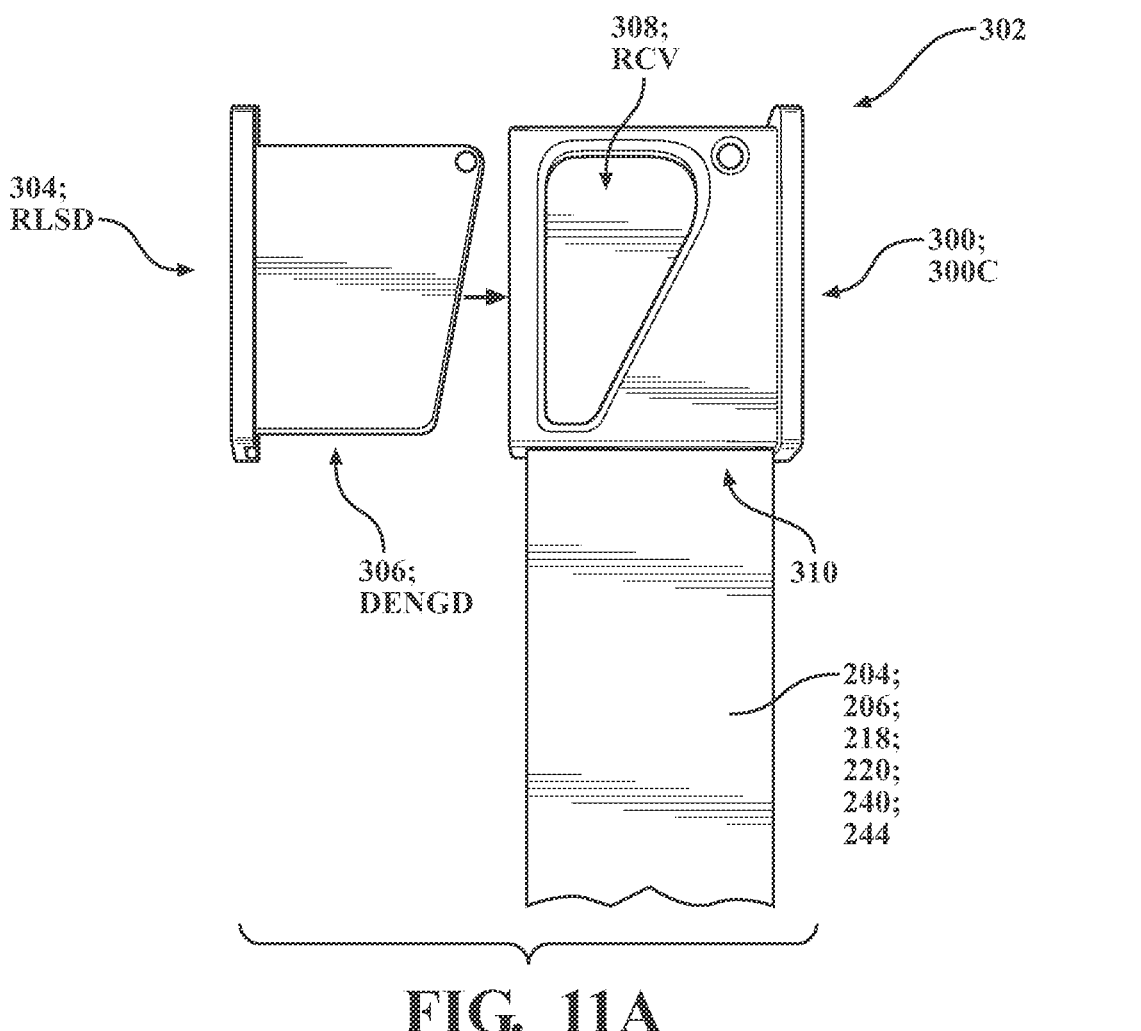
FIGS. 11A-11C are perspective views illustrating an operation of the strap management guard of FIGS. 10A and 10B.
Figure 11C:
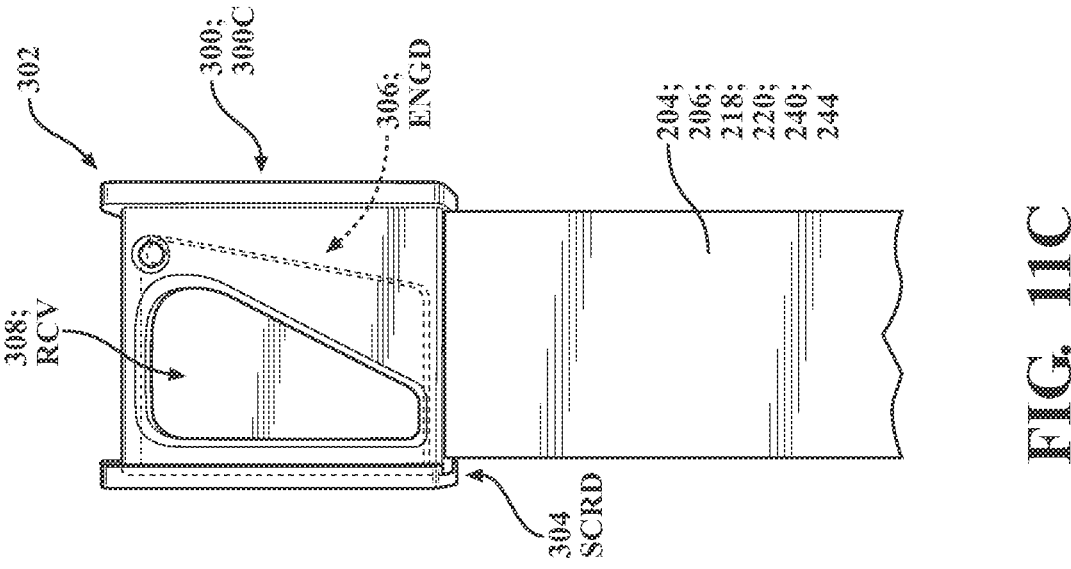

The released position RLSD of the keeper 304 of the door strap management guard 300A is shown in FIGS. 6 and 7A-7B and the secured position SCRD of keeper 304 of the door strap management guard 300A is shown in FIG. 7C. The released position RLSD of the keeper 304 of the cam strap management guard 300B is shown in FIGS. 8 and 9A and the secured position SCRD of the keeper 304 of the cam strap management guard 300B is shown in FIG. 9B. The released position RLSD of the keeper 304 of the slider strap management guard 300C is shown in FIGS. 10A-10B and 11A and the secured position SCRD of the keeper 304 of the slider strap management guard 300C is shown in FIGS. 10C and 11C.

The retainer 306 is operable between an engaged configuration ENGD and a disengaged configuration DENGD. In the engaged configuration ENGD, the retainer 306 retains the keeper 304 in the secured position SCRD. Specifically, in the engaged configuration ENGD, the receiver 314 secures the protrusion 312 to retain the keeper 304 in the secured position SCRD. In the disengaged configuration DENGD, the retainer 306 permits movement of the keeper 304 between the secured position SCRD and the released position RLSD. Specifically, in the disengaged configuration DENGD, the receiver 314 is spaced from the protrusion 312 to permit movement of the keeper 304 between the secured position SCRD and the released position RLSD. In other words, in the engaged configuration ENGD, the keeper 304 is retained in the secured position SCRD and a user of the strap management guard 300 is inhibited from removing the strap 204, 206, 218, 220, 240, 244 from the channel 308. In the disengaged configuration DENGD, the keeper 304 is permitted to move from the secured position SCRD to the released position RLSD, where a user of the strap management guard 300 may remove the strap 204, 206, 218, 220, 240, 244 from the channel 308.

The engaged configuration ENGD of the retainer 306 of the door strap management guard 300A is shown in FIG. 7C and the disengaged configuration DENGD of the retainer 306 of the door strap management guard 300A is shown in FIGS. 6 and 7A-7B. The engaged configuration ENGD of the retainer 306 of the cam strap management guard 300B is shown in FIG. 9B and the disengaged configuration DENGD of the retainer 306 of the cam strap management guard 300B is shown in FIGS. 8 and 9A. The engaged configuration ENGD of the retainer 306 of the slider strap management guard 300C is shown in FIGS. 10C and 11C and the disengaged configuration DENGD of the retainer 306 of the slider strap management guard 300C is shown in FIGS. 10A-10B and 11A-11B.

Referring back to FIGS. 6 and 7A-7C, the door strap management guard 300A will be described in greater detail below. As shown in FIG. 6, the keeper 304 of the door strap management guard 300A is pivotably coupled to the base 302 along an axis DSAX located at a first end 316 of the base 302. The first end 316 of the base 302 opposes a second end 317 of the base 302, with the inlet 310 being adjacent to the second end 317. Referring now to FIGS. 7A-7C, the keeper 304 is configured to pivot about the axis DSAX between the released position RLSD and the secured position SCRD, the keeper 304 being in the released position RLSD in FIGS. 7A and 7B and in the secured position SCRD in FIG. 7C.

Movement of the keeper 304 from the released position RLSD to the secured position SCRD transitions the retainer 306 from the disengaged configuration DENGD to the engaged configuration ENGD. As shown in FIG. 7A, the retainer 306 operates in the disengaged configuration DENGD, where the receiver 314 is spaced from the protrusion 312, permitting movement of the keeper 304 between the secured position SCRD and the released position RLSD. As shown in FIG. 7C, the retainer 306 operates in the engaged configuration ENGD, where the receiver 314 secures the protrusion 312 to retain the keeper 304 in the secured position SCRD.

In some instances, such as the instance of FIG. 6, the door strap management guard 300A may include an abutment 318 to at least partially limit movement of the strap 204, 206, 218, 220, 240, 244. The abutment 318 limits movement of the strap 204, 206, 218, 220, 240, 244 during operation of the channel 308 in the received configuration RCV. As shown in FIG. 5, the base 302 includes the abutment 318. Correspondingly, the strap 204, 206, 218, 220, 240, 244 includes an aperture 320 that is sized and shaped to receive the abutment 318. Referring to FIG. 7A, during operation of the channel 308 in the received configuration RCV, the aperture 320 receives the abutment 318 and the abutment 318 is configured to at least partially limit movement of the strap 204, 206, 218, 220, 240, 244 relative to the channel 308.

Figures 12A, 12B, 13:
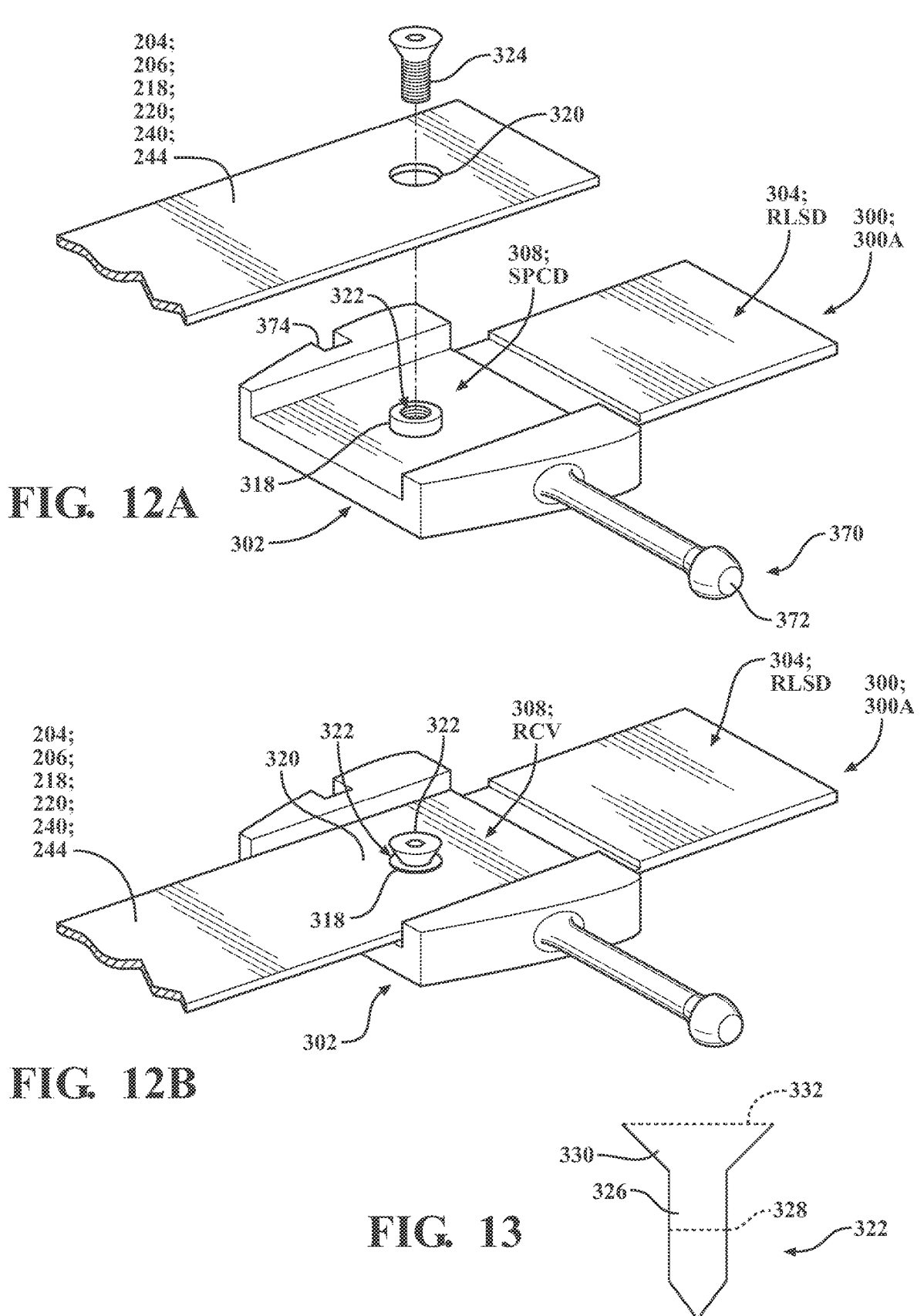
FIGS. 12A-12B are perspective views of a fourth instance of the strap management guard of the patient support system in FIGS. 1-4.
FIG. 13 is a diagrammatic view of an insert for use with the strap management guard of FIGS. 12A and 12B.

In further instances of the door strap management guard 300A, such as the instance of FIGS. 12A-12B, the abutment 318 of the door strap management guard 300A may include an insert 322 configured to receive a fastener 324. The fastener 324 provides a means of securing the strap 204, 206, 218, 220, 240, 244 to the base 302. Referring to FIG. 13, the fastener 324 may include a shaft 326 that is configured to be received by the insert 322. For instance, the shaft 326 may include a shaft width 328 that allows the shaft 326 to be received by the insert 322. The fastener 324 may also include a head 330 configured to secure the strap 204, 206, 218, 220, 240, 244 to the base 302 during operating of the channel 308 in the received configuration RCV (shown in FIG. 12B). As shown in FIG. 13, the head 330 may include a head width 332 that allows the head 330 to secure the strap 204, 206, 218, 220, 240, 244 to the base 302 while the channel 308 receives a portion of the strap 204, 206, 218, 220, 240, 244.

Referring back to FIGS. 8 and 9A-9B, the cam strap management guard 300B will be described in greater detail below. As shown in FIG. 8, the keeper 304 of the cam strap management guard 300B is pivotably coupled to the base 302 along an axis CAX located between a first end 316 of the base 302 and an opposing second end 317 of the base 302. As shown in FIG. 8, the inlet 310 is adjacent to the second end 317 of the base 302. Referring now to FIGS. 9A-9B, the keeper 304 is configured to pivot about the axis CAX between the released position RLSD and the secured position SCRD, the keeper 304 being in the released position RLSD in FIG. 9A and the secured position SCRD in FIG. 9B.

Movement of the keeper 304 from the released position RLSD to the secured position SCRD transitions the retainer 306 from the disengaged configuration DENGD to the engaged configuration ENGD. As shown in FIG. 9A, the retainer 306 operates in the disengaged configuration DENGD, where the receiver 314 is spaced from the protrusion 312, permitting movement of the keeper 304 between the secured position SCRD and the released position RLSD. As shown in FIG. 9B, the retainer 306 operates in the engaged configuration ENGD, where the receiver 314 secures the protrusion 312 to retain the keeper 304 in the secured position SCRD.

In the instance of the cam strap management guard 300B shown in FIGS. 8 and 9A-9B, the keeper 304 includes teeth 338. The teeth 338 may be configured to further restrict movement of the strap 204, 206, 218, 220, 240, 244 when the keeper 304 operates in the secured position. Specifically, when a user attempts to remove the strap 204, 206, 218, 220, 240, 244 from the channel 308 during operation of the retainer 306 the engaged configuration ENGD, the teeth 338 may provide an opposing force (to the force exerted by the user when the user attempts to remove the strap), such as a frictional force.

Figure 11B:
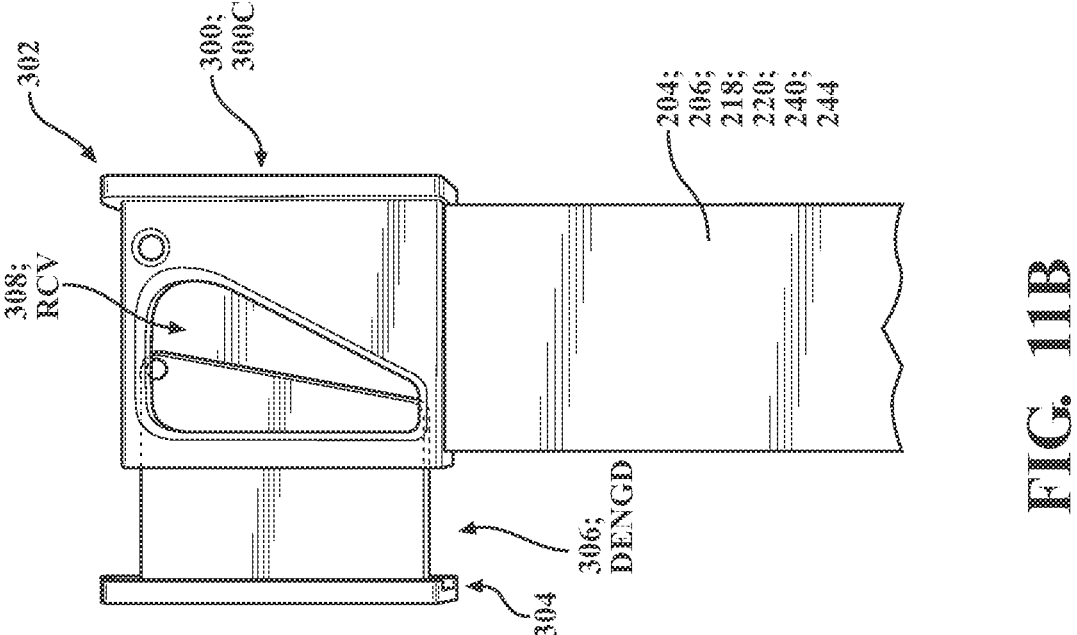

Referring back to FIGS. 10A-10C and 11A-11C, the slider strap management guard 300C will be described in greater detail below. As shown in FIGS. 10A and 10B, the base 302 of the slider strap management guard 300C may include a second inlet 340. In the instance of the slider strap management guard 300C shown in FIGS. 10A-10C and 11A-11C, the second inlet 340 is orthogonal to the first inlet 310. As shown in FIGS. 11A-11C, the channel 308 is arranged to receive the keeper 304 therein via the second inlet 340, and to receive the strap 204, 206, 218, 220, 240, 244 therein via the first inlet 310.

As shown in FIGS. 10A and 10B, the receiver 314 of the slider strap management guard 300C may extend within the channel 308 in a manner that is parallel to the first inlet 340. As shown, the receiver 314 extends longitudinally within the channel 308 from a first end 342 to a second end 344 of the base 302. As is best shown in FIG. 10C, the base 302 may include more than one receiver 314 extending within the channel 308.

As shown in FIG. 10B, the protrusion 312 of the slider strap management guard 300C may extend longitudinally from a first end 346 to a second end 348 of the keeper 304. As is best shown in FIG. 10C, the keeper 304 may include more than one protrusion 312.

Referring to FIGS. 11A-11C, during operation of the retainer 306 in the engaged configuration ENGD, the channel 308 receives the keeper 304 therein via the second inlet 340. As such, the receiver 314 secures the protrusion 312 to retain the keeper 304 in the secured position. Specifically, as the channel 308 receives the keeper 304, the receivers 314 slidably receives the protrusions 312, transitioning the retainer 306 from the disengaged configuration DENGD (shown in FIG. 11A) to the engaged configuration ENGD (shown in FIG. 11C). Referring to FIG. 10C, during operation of the retainer 306 in the engaged configuration ENGD, the channel 308 also receives the proximal end of the strap 204, 206, 218, 220, 240, 244 therein via the first inlet 310 such that the proximal end of the strap 204, 206, 218, 220, 240, 244 is disposed between the receivers 314 and the protrusions 312. As such, when the receivers 314 receive and secure the protrusions 312 during the engaged configuration ENGD, the receivers 314 retain the keeper 304 in the secured position SCRD, restricting movement of the strap 204, 206, 218, 220, 240, 244 out of the channel 308.

Figure 14A:
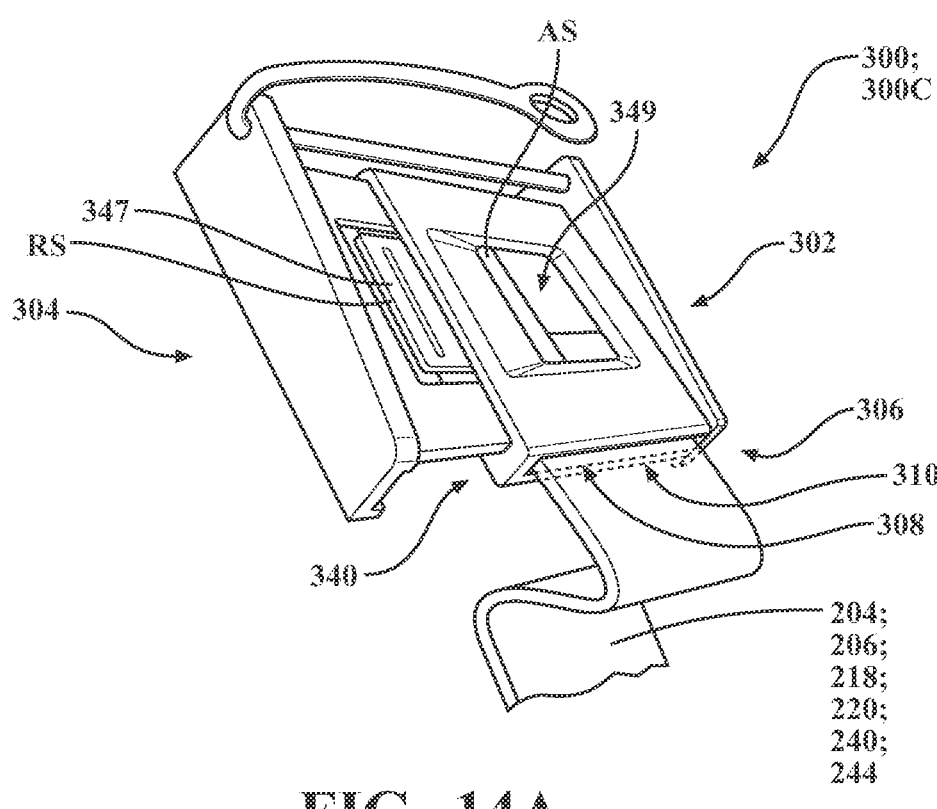
FIG. 14A is a perspective view of a fifth instance of the strap management guard of the patient support system in FIGS. 1-4.
Figure 14B:
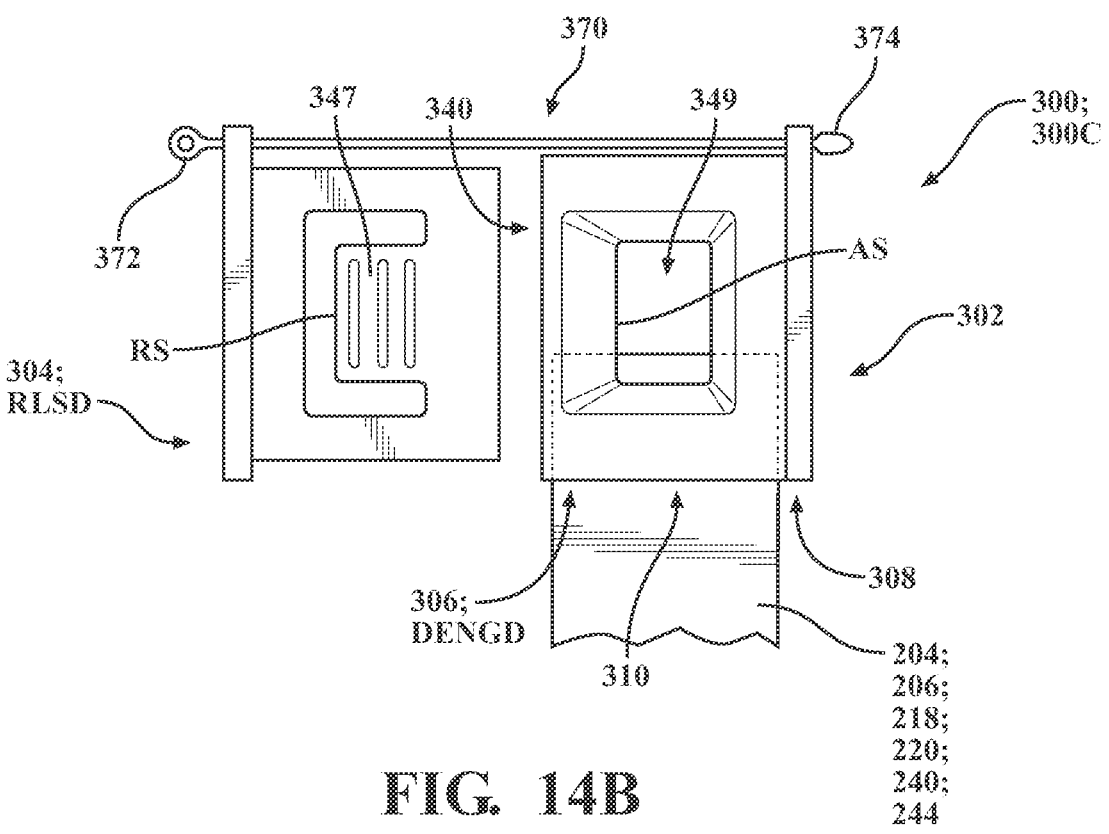
FIGS. 14B-14C are top views of the strap management guard of FIG. 14A.
Figure 14C:
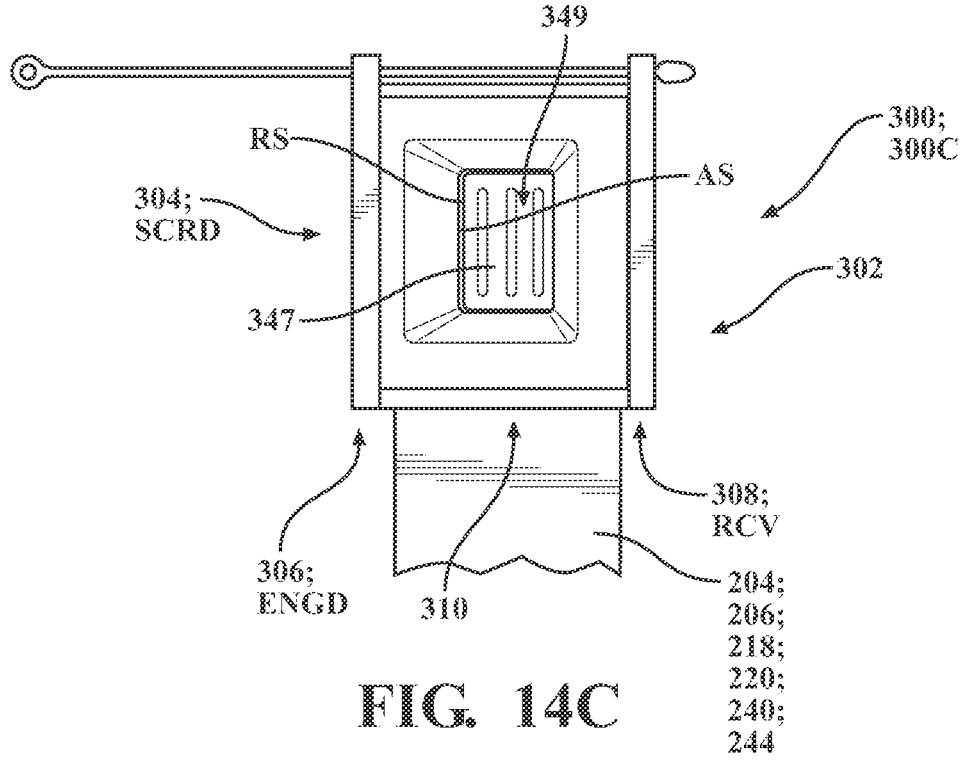

In another instance of the slider strap management guard 300C shown in FIGS. 14A-14D, the keeper 304 may additionally include a flange 347 including a retaining surface RS. Furthermore, the base 302 may additionally include a slot 349 extending orthogonally to the first inlet 310, the slot 349 including an abutment surface AS. Referring to FIG. 14C, during operation of the retainer 306 in the engaged configuration ENGD, the channel 308 receives the flange 347 therein via the second inlet 340 such that the abutment surface AS contacts the retaining surface RS to retain the keeper 304 in the secured position SCRD.

Figure 14D:
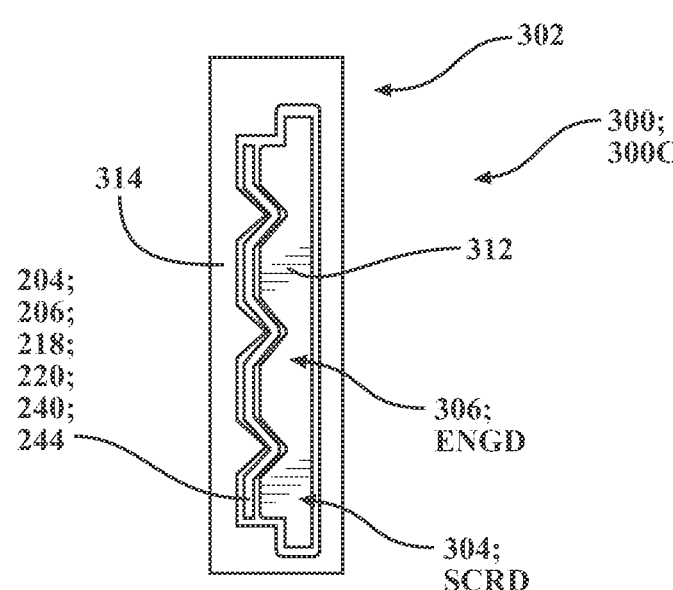
FIG. 14D is a cutaway view of the strap management guard of FIG. 14A.

It should be noted that the flange 347 and the slot 349 of the instance of the slider strap management guard 300C shown in FIGS. 14A-14D aid in retaining the keeper 304 in the secured position SCRD. As shown in FIG. 14D, the instance of the slider strap management guard 300C also includes the previously described receivers 314 and protrusions 312. As such, during operation of the retainer 306 in the engaged configuration ENGD, the receiver 314 secures the protrusion 312 to retain the keeper 304 in the secured position SCRD, and the abutment surface AS of the flange 347 contacts the retaining surface RS of the slot 349 to aid in retaining the keeper 304 in the secured position SCRD.

A construction of the slider strap management guard 300C may vary. For example, additional alternate instances of the slider strap management guard 300C are shown in FIGS. 15A-17C. A first alternate instance of the slider strap management guard 300C is shown in FIGS. 15A-15D, a second alternate instance of the slider strap management guard 300C is shown in FIGS. 16A-16B, and a third alternate instance of the slider strap management guard 300C is shown in FIGS. 17A-17B.

Figure 15A:
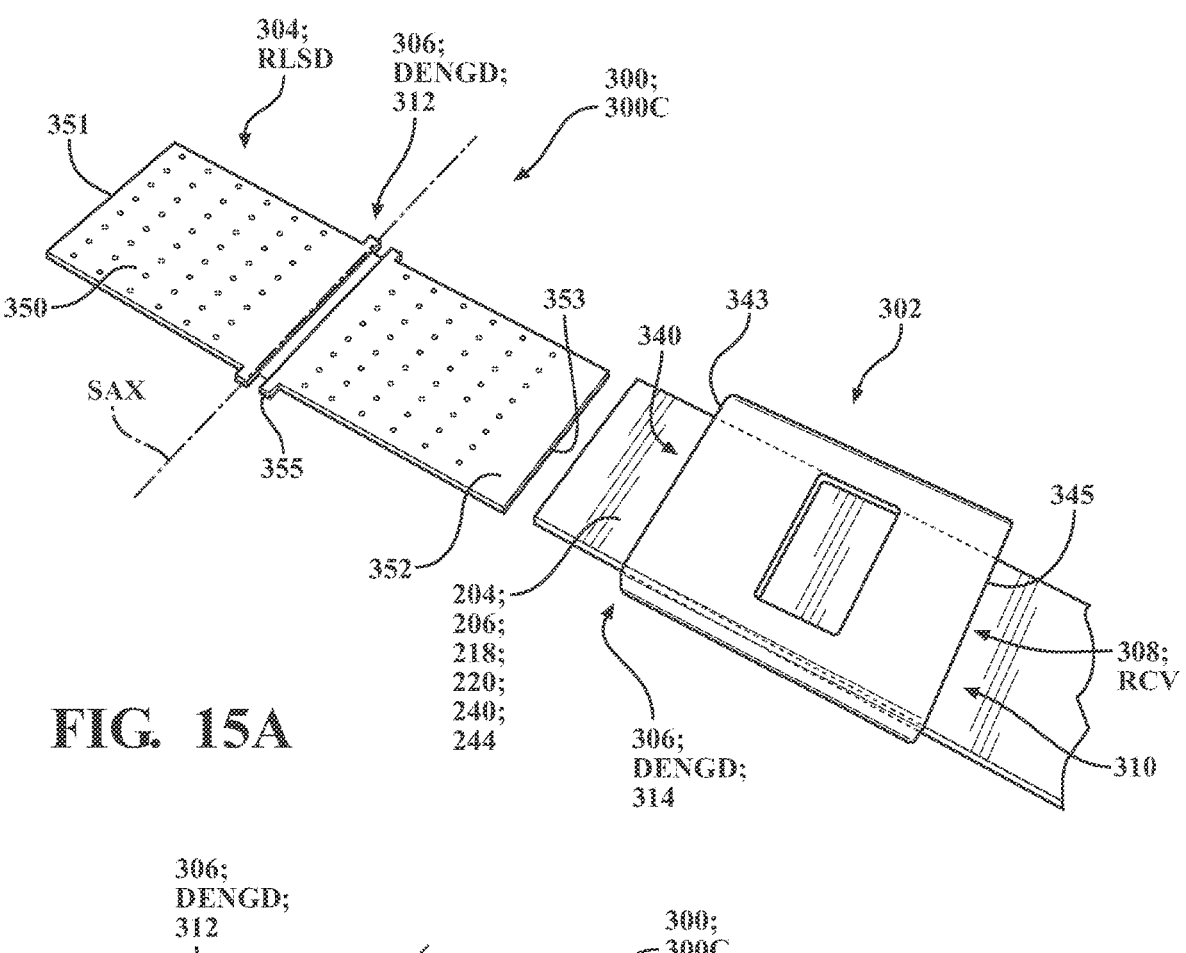
FIGS. 15A-15D illustrate an operation of a sixth instance of the strap management guard of the patient support system in FIGS. 1-4.
Figure 15B:
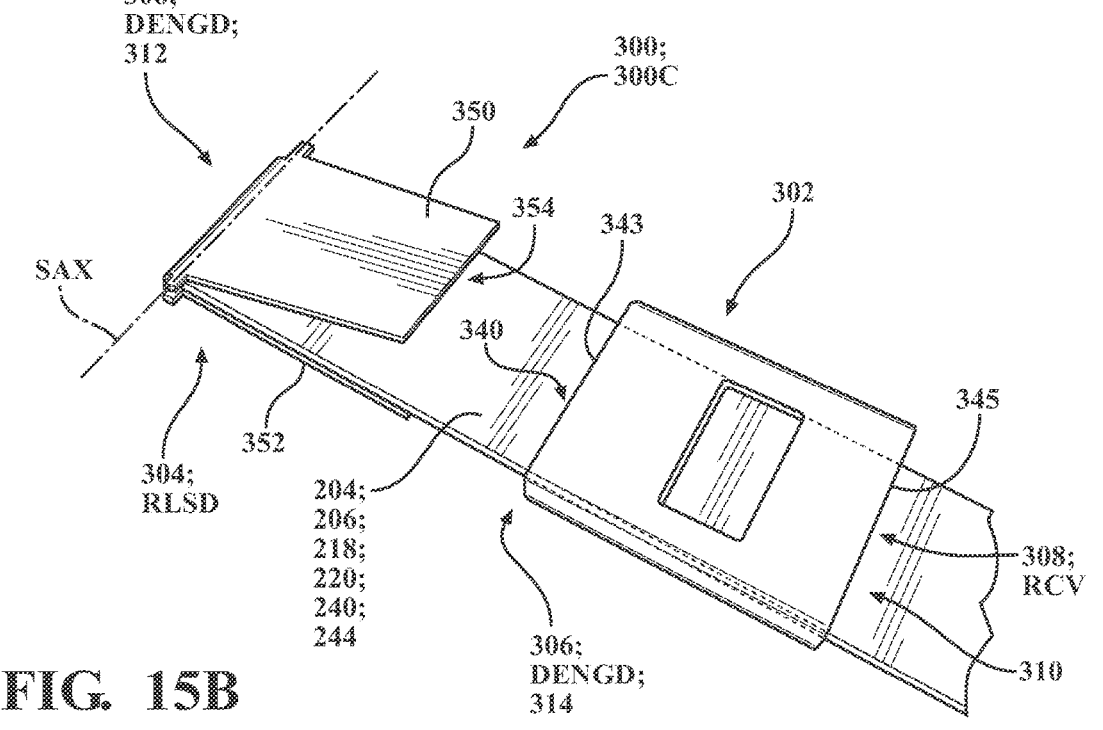
Figure 15C:
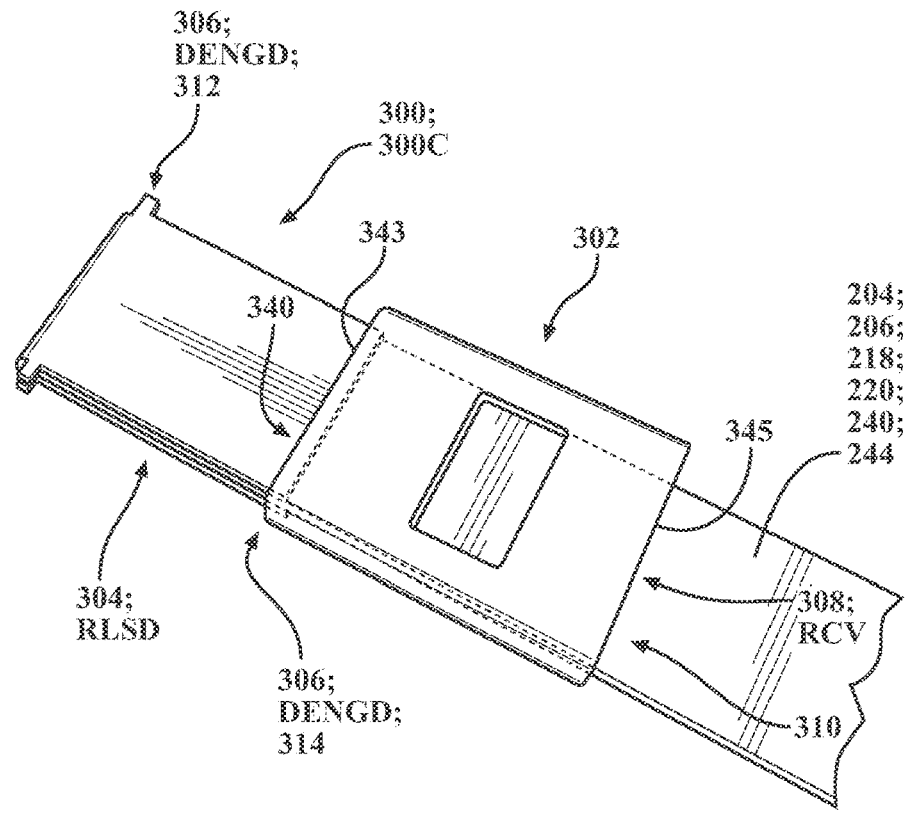
Figure 15D:
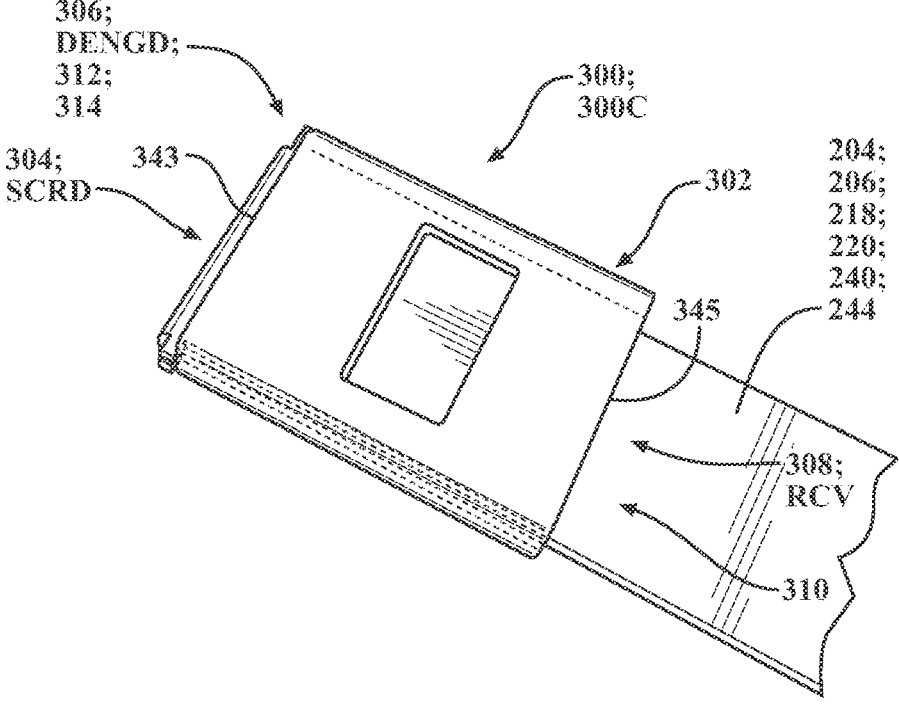
Figures 16A, 16B:
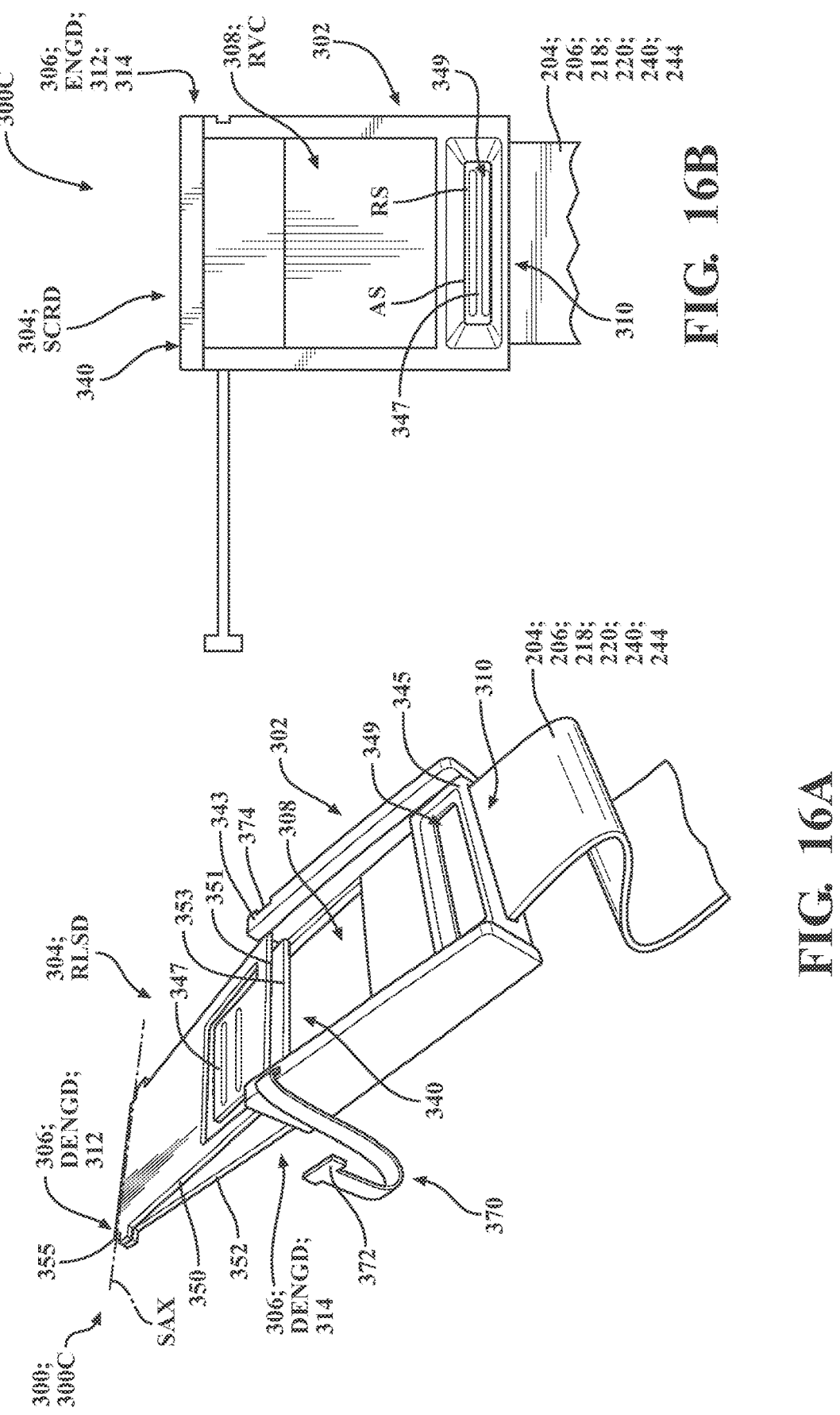
FIG. 16A is a perspective view of a seventh instance of the strap management guard of the patient support system in FIGS. 1-4.
FIG. 16B is a top view of the strap management guard of FIG. 16A
Figures 17A, 17B:
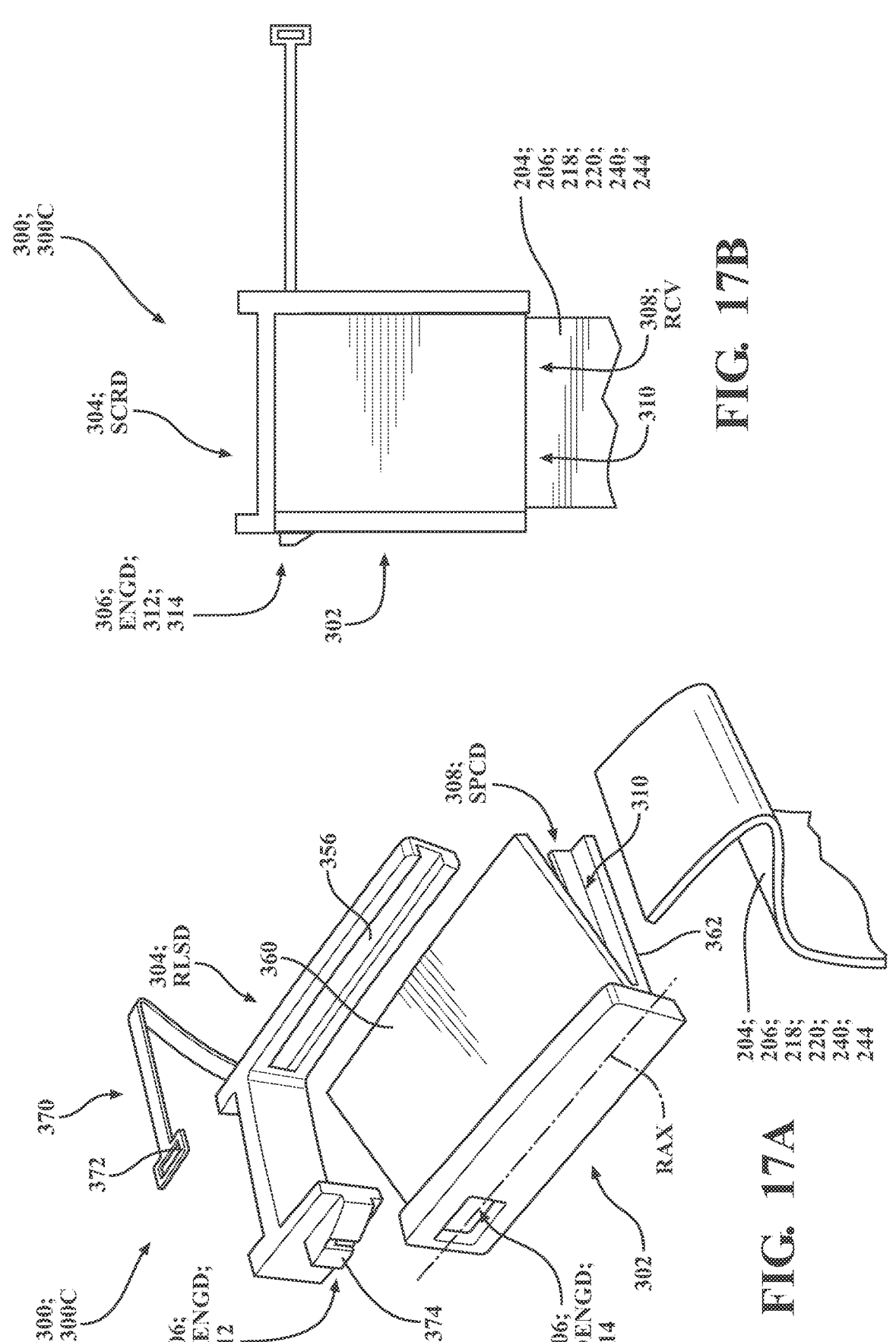
FIG. 17A is a perspective view of an eighth instance of the strap management guard of the patient support system in FIGS. 1-4.
FIG. 17B is a top view of the strap management guard of FIG. 17A

As shown in FIGS. 15A-15D and 16A-16B, the keeper 304 of the first and second alternate instance of the slider strap management guard 300C defines a pocket 354. As shown, the keeper 304 includes a first portion 350 and a second portion 352, which are in pivotable relation about an axis SAX located at a point 355 between ends 351, 353 of the keeper 304. As shown in FIGS. 15B and 16A, the first portion 350 and/or the second portion 352 pivot about the axis SAX to define a pocket 354. Referring to FIGS. 15B and 16B, the pocket 354 is configured to receive the proximal end of the strap 204, 206, 218, 220, 240, 244.

Additionally, the base 302 of the first and second alternate instance of the slider strap management guard 300C includes a second inlet 340 adjacent to a second end 343 of the base 302. As shown in FIGS. 15A and 16A, the second end 343 opposes a first end 345 of the base 302, with the first inlet 310 being adjacent to the first end 345 such that the second inlet 340 is parallel to the first inlet 310. Referring to FIGS. 15C and 16B, the channel 308 is arranged to receive the keeper 304 therein via second inlet 340, and to receive the strap 204, 206, 218, 220, 240, 244 therein via the first inlet 310. Specifically, the channel 308 is sized and shaped to receive the first portion 350 and the second portion 352 of the keeper 304 when the first portion 350 and/or second portion 352 are pivoted about the axis SAX such that the first portion 350 is disposed above the second portion 352.

Referring to FIGS. 15A-15D and 16A-16B, during operation of the retainer 306 in the engaged configuration ENGD, the channel 308 receives the keeper 304 therein via the second inlet 340. As such, the receiver 314 secures the protrusion 312 to retain the keeper 304 in the secured position. Referring to FIGS. 15C and 16B, the pocket 354 of the keeper 304 receives the proximal end of the strap 204, 206, 218, 220, 240, 244 while the channel 308 receives the keeper 304 therein. As such, during operation of the retainer 306 in the engaged configuration ENGD, the channel 308 also receives the proximal end of the strap 204, 206, 218, 220, 240, 244. As such, when the receiver 314 receives and secures the protrusion 312 during the engaged configuration ENGD (as shown in FIGS. 15D and 16B), the receiver 314 retains the keeper 304 in the secured position SCRD, restricting movement of the strap 204, 206, 218, 220, 240, 244 out of the channel 308.

In the first alternate instance of the slider strap management guard 300C, a size of the keeper 304 and a size of the channel 308 aids in retaining the keeper 304 in the secured position SCRD. Specifically, a size of the first portion 350, the second portion 352, and the channel 308 may be selected such that, when a user attempts to remove the strap 204, 206, 218, 220, 240, 244 from the channel 308 during operation of the retainer 306 the engaged configuration ENGD, the keeper 304 and the channel 308 together may provide an opposing force (to the force exerted by the user when the user attempts to remove the strap), such as a frictional force.

In the second alternate instance of the slider strap management guard 300C, the keeper 304 may additionally include a flange 347 including a retaining surface RS (the retaining surface RS notated in FIG. 16B). Furthermore, the base 302 may additionally include a slot 349 extending parallelly to the first inlet 310, the slot 349 including an abutment surface AS (the retaining surface RS notated in FIG. 16B). Referring to FIG. 16B, during operation of the retainer 306 in the engaged configuration ENGD, the channel 308 receives the flange 347 therein via the second inlet 340 such that the abutment surface AS contacts the retaining surface RS to retain the keeper 304 in the secured position SCRD.

It should be noted that the flange 347 and the slot 349 of the second alternate instance of the slider strap management guard 300C aid in retaining the keeper 304 in the secured position SCRD. As shown in FIG. 16B, the second alternate instance of the slider strap management guard 300C also includes the previously described receivers 314 and protrusions 312. As such, during operation of the retainer 306 in the engaged configuration ENGD, the receiver 314 secures the protrusion 312 to retain the keeper 304 in the secured position SCRD, and the abutment surface AS of the flange 347 contacts the retaining surface RS of the slot 349 to aid in retaining the keeper 304 in the secured position SCRD.

It should be noted that, in the instance of the first alternate instance of the slider strap management guard 300C and in the instance of the second alternate instance of the slider strap management guard 300C, the receiver 314 is illustrated as a surface configured to abut the protrusion 312 during operation of the retainer 306 the engaged configuration ENGD. However, in other instances, the receiver 314 of the first alternate instance of the slider strap management guard 300C may be provided as a receptacle for receiving the protrusion 312. In still other instances, the receiver 314 and the protrusion 312 may be optionally omitted.

As shown in FIG. 17A, the keeper 304 of the third alternate instance of the slider strap management guard 300C includes a groove 356. Additionally, the base 302 includes a first portion 360 and a second portion 362, which are in pivotable relation about an axis BAX located at an end of the base 302. The groove 356 is arranged to receive both the first portion 360 and the second portion 362 during operation of the retainer 306 in the engaged configuration ENGD. Specifically, the groove 356 is sized and shaped to receive the first portion 360 and the second portion 362 of the base 302 when the first portion 360 and/or second portion 362 are pivoted about the axis BAX such that the first portion 360 is disposed above the second portion 362.

Referring to FIG. 17B, in the third alternate instance of the slider strap management guard 300C, the groove 356 is configured to slidably receive the first portion 360 and the second portion 362 of the base 302 until the receiver 314 receives and secures the protrusion 312. In this way, the retainer 306 is transitioned from the disengaged configuration DENGD (shown in FIG. 17A) to the engaged configuration ENGD (shown in FIG. 17B). Referring to FIG. 17B, during operation of the retainer 306 in the engaged configuration ENGD, the channel 308 also receives the proximal end of the strap 204, 206, 218, 220, 240, 244 therein via the inlet 310 such that the proximal end of the strap 204, 206, 218, 220, 240, 244 is disposed between the first portion 360 and the second portion 362. As such, when receiver 314 receives and secures the protrusion 312 during the engaged configuration ENGD, the receiver 314 retains the keeper 304 in the secured position SCRD, restricting movement of the strap 204, 206, 218, 220, 240, 244 out of the channel 308.

As shown in FIGS. 12A, 14B, 16A, and 17A, the strap management guard 300 may include a tether lock 370. The tether lock 370 is configured to manages an excess length of a strap to which the strap management guard 300 is removably attached.

Figure 18B:
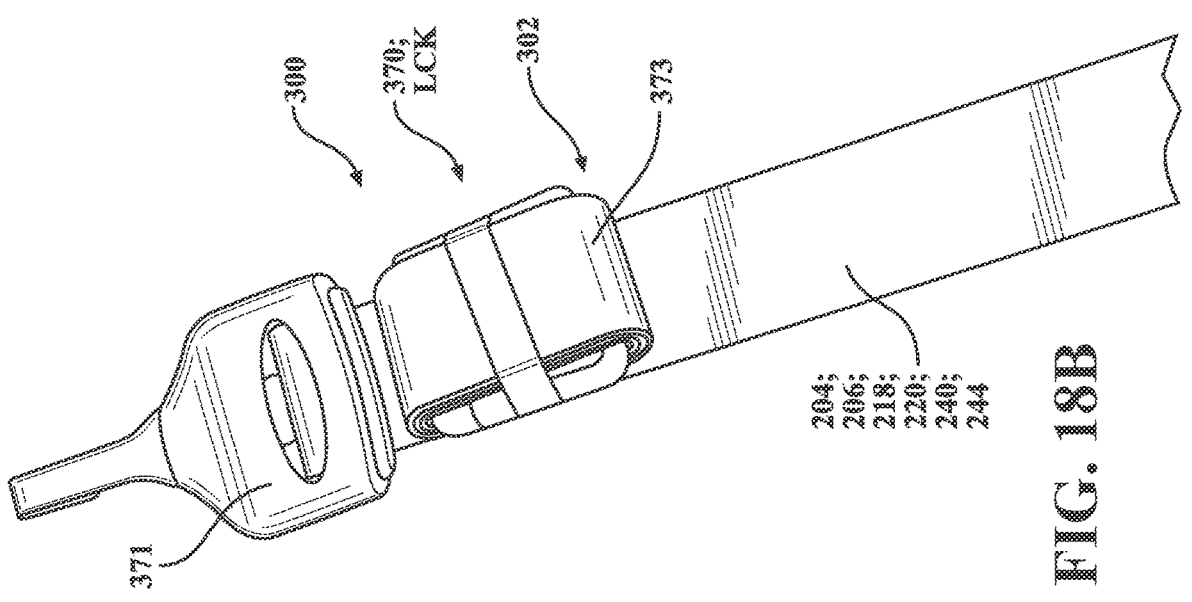
FIG. 18B is a perspective view of an instance of the strap management guard of the patient support system in FIGS. 1-4, wherein the strap management guard includes a tether lock.
Figure 18A:
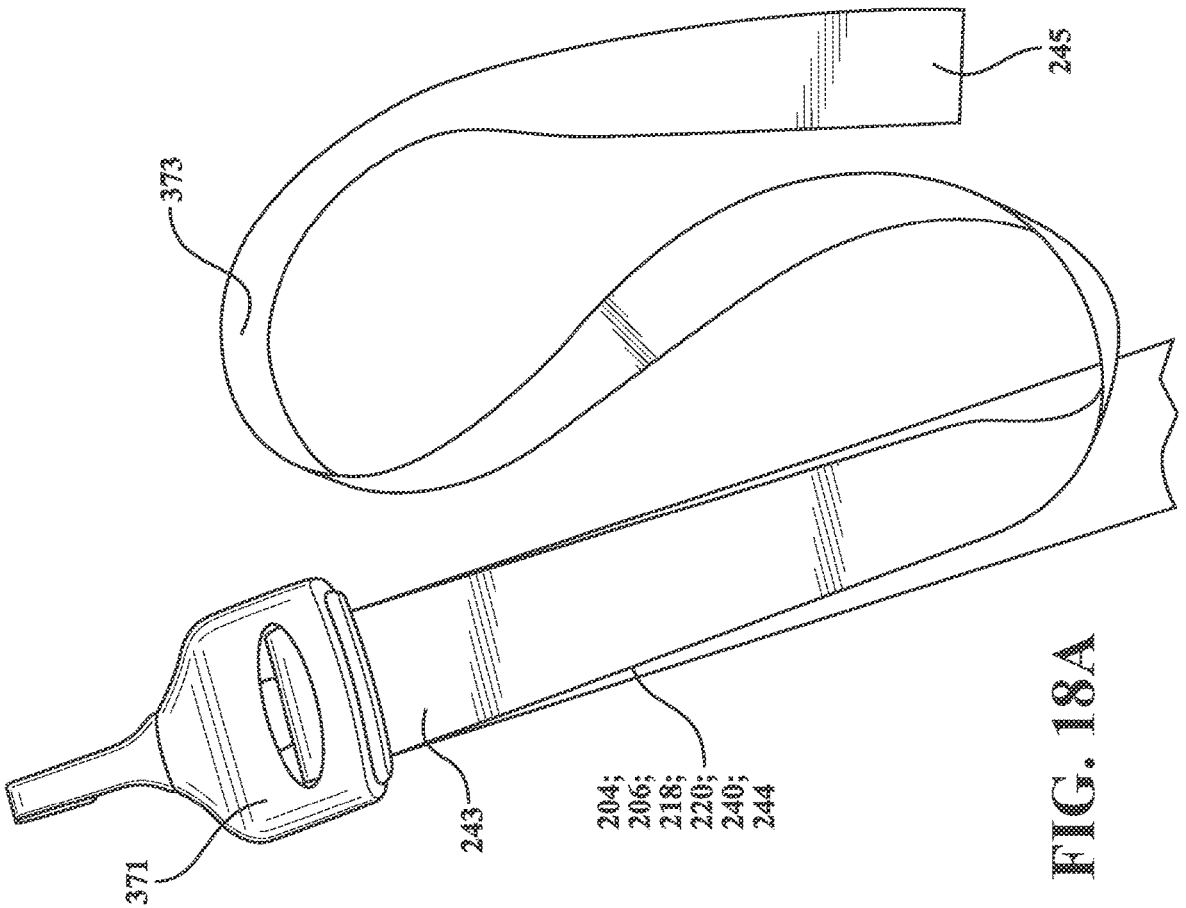
FIG. 18A is a perspective view of an excess length of a strap of the patient support system in FIGS. 1-4.

A portion of a strap is determined to be an excess length in instances where the portion is unnecessary for coupling the strap to and enabling proper use of a connector, a coupling bracket, or a latch. For example, referring to FIG. 2, the first connector 228 is able to be coupled to the first lower strap 204 and the connectors 228, 230 are able to cooperate to facilitate releasably attaching the first lower strap 204 and second lower strap 206 together. Therefore, a portion of the first lower strap 204 that is unnecessary for coupling the first lower strap 204 to and enabling proper use of the first connector 228 is determined to be an excess length. A second example of an excess length is shown in FIG. 18A. As shown in FIG. 18A, the portion 373 of the strap 204, 206, 218, 220, 240, 244 may be determined to be an excess length (assuming connector 371 is able to be used properly) as the portion 373 of the strap 204, 206, 218, 220, 240, 244 is unnecessary for coupling the strap 204, 206, 218, 220, 240, 244 to the connector 371.

To manage an excess length of a strap, the tether lock 370 is configured to operate in a locked configuration where the tether lock 370 secures a portion of the strap to which the strap management guard 300 is removably attached. Specifically, during the locked configuration, the tether lock 370 secures a portion of a strap disposed between the base 302 and the tether lock 370. In this way, the tether lock 370 manages an excess length of a strap. For example, referring to FIG. 18B, the tether lock 370 is operating in the locked configuration LCK where the tether lock 370 secures the portion of the strap 204, 206, 218, 220, 240, 244 disposed between the base 302 and the tether lock 370.

A portion of a strap may be disposed between the base 302 and the tether lock 370 using a variety of methods. In one example, the strap management guard 300 is removably attached to the proximal end 245 (shown in FIG. 18A) of the strap 204, 206, 218, 220, 240, 244 and the strap management guard 300 is rolled along the strap 204, 206, 218, 220, 240, 244 toward the distal end 243 of the strap 204, 206, 218, 220, 240, 244. It should be noted that, in other instances, a portion of a strap may be disposed between the base 302 and the tether lock 370 using a different method.

Once a portion of the strap is disposed between the base 302 and the tether lock 370, the tether lock 370 may operate in the locked configuration LCK to secure the portion of the strap disposed between the base 302 and the tether lock 370. In the instance of FIG. 18B, the tether lock 370 is illustrated as an elastic band, which may expand to receive the portion of the strap and the base 302 and contract to secure the portion of the strap to the base 302. In other instances, such as the instances of FIGS. 12A, 14B, 16A, and 17A, the tether lock 370 may include a latch 372 and a catch 374 to secure the portion of the strap disposed between the base 302 and the tether lock 370. In such instances, during operation of the tether lock 370 in the locked configuration LCK, the catch 374 secures the latch 372 to at least partially limit movement of the latch 372 relative to the catch 374. In other words, once a portion of the strap is disposed between the base 302 and the tether lock 370, the catch 374 secures the latch 372 to secure the portion of the strap to the base 302.

Several configurations have been discussed in the foregoing description. However, the configurations discussed herein are not intended to be exhaustive or limit the invention to any particular form. The terminology which has been used is intended to be in the nature of words of description rather than of limitation. Many modifications and variations are possible in light of the above teachings, and the invention may be practiced otherwise than as specifically described.

What is claimed is:

1. A harness assembly for use with a patient transport apparatus, the harness assembly comprising:

a strap for securing a patient to the patient transport apparatus, the strap defining a distal end with a strap interface for attaching to the patient transport apparatus, and a proximal end; and a guard configured for removable attachment to the proximal end of the strap to secure the guard to the proximal end of the strap for concurrent movement with the proximal end of the strap relative to the strap interface, the guard including:

a base defining a channel arranged to receive and secure the proximal end of the strap therein;

a keeper arranged for movement relative to the base between:

a released position to permit movement of the proximal end of the strap along the channel of the base, and a secured position to inhibit movement of the proximal end of the strap out of the channel; and a retainer coupled between the base and the keeper and being movable relative to the keeper between:

an engaged configuration to retain the keeper in the secured position, and a disengaged configuration to permit movement of the keeper between the secured position and the released position.

2. The harness assembly of claim 1, wherein the channel of the base defines an inlet, the channel being arranged to receive the proximal end of the strap therein via the inlet.

3. The harness assembly of claim 2, wherein the retainer includes:

a protrusion coupled to the keeper; and a receiver formed in the base shaped to receive the protrusion.

4. The harness assembly of claim 3, wherein, during operation of the retainer in the engaged configuration, the receiver secures the protrusion to retain the keeper in the secured position.

5. The harness assembly of claim 3, wherein, during operation of the retainer in the disengaged configuration, the receiver is spaced from the protrusion to permit movement of the keeper between the secured position and the released position.

6. The harness assembly of claim 3, wherein the keeper is pivotably coupled to the base along an axis, the keeper being configured to pivot about the axis between the released position and the secured position.

7. The harness assembly of claim 3, wherein the channel is operable between:

a received configuration where the channel receives the proximal end of the strap; and a spaced configuration where the channel is spaced from the proximal end of the strap.

8. The harness assembly of claim 7, wherein the base includes an abutment, wherein the proximal end of the strap includes an aperture sized and shaped to receive the abutment, and wherein, during operation of the channel in the received configuration, the aperture receives the abutment and the abutment is configured to at least partially limit movement of the strap relative to the channel.

9. The harness assembly of claim 8, wherein the abutment of the base includes an insert configured to receive a fastener, the fastener including a shaft configured to be received by the insert; and wherein the fastener includes a head, the head being configured to secure the strap to the base when the shaft is received by the insert and during operation of the channel in the received configuration.

10. The harness assembly of claim 3, wherein the inlet is further defined as a first inlet, and wherein the channel of the base defines a second inlet parallel to the first inlet, the channel being arranged to receive the keeper therein via the second inlet.

11. The harness assembly of claim 10, wherein the receiver is adjacent to the second inlet, and wherein, during operation of the retainer in the engaged configuration, the channel receives the keeper therein via the second inlet such that the receiver secures the protrusion to retain the keeper in the secured position.

12. The harness assembly of claim 10, wherein the keeper includes a flange including a retaining surface, wherein the base includes a slot including an abutment surface, and wherein the slot extends parallelly to the first inlet and configured to receive the flange, during operation of the retainer in the engaged configuration, such that the abutment surface contacts the retaining surface to retain the keeper in the secured position.

13. The harness assembly of claim 3, wherein the inlet is further defined as a first inlet, wherein the receiver extends within the channel parallel to the first inlet, and wherein the channel of the base defines a second inlet orthogonal to the first inlet, the channel being arranged to receive the keeper therein via the second inlet.

14. The harness assembly of claim 13, wherein, during operation of the retainer in the engaged configuration, the channel receives the keeper therein via second inlet such that the receiver secures the protrusion to retain the keeper in the secured position.

15. The harness assembly of claim 13, wherein the keeper includes a flange including a retaining surface, wherein the base includes a slot including an abutment surface, wherein the slot extends orthogonally to the first inlet, and wherein the channel is arranged to receive the flange therein via the second inlet, during operation of the retainer in the engaged configuration, such that the abutment surface contacts the retaining surface to retain the keeper in the secured position.

16. The harness assembly of claim 1, wherein the base further includes a first portion and a second portion, the first portion and second portion defining the channel, and wherein the keeper includes a groove arranged to receive both the first portion and the second portion during operation of the retainer in the engaged configuration.

17. The harness assembly of claim 1, further comprising a tether lock configured to operate in a locked configuration where the tether lock secures a portion of the strap, wherein the tether lock includes a latch and a catch arranged to secure the latch to at least partially limit movement of the latch relative to the catch during operation of the tether lock in the locked configuration.

18. The harness assembly of claim 1, wherein the keeper defines a pocket configured to receive the proximal end of the strap.

19. A harness assembly for use with a patient transport apparatus, the harness assembly comprising:

a strap for securing a patient to the patient transport apparatus, the strap defining a distal end with a strap interface for attaching to the patient transport apparatus, and a proximal end; and a guard configured for removable attachment to the proximal end of the strap, the guard including:

a base including a first portion and a second portion, the first portion and the second portion defining a channel arranged to receive the proximal end of the strap therein;

a keeper being arranged for movement relative to the base between:

a released position to permit movement of the proximal end of the strap along the channel of the base, and a secured position to restrict movement of the proximal end of the strap out of the channel; and a retainer coupled between the base and the keeper and being operable between:

an engaged configuration to retain the keeper in the secured position, and a disengaged configuration to permit movement of the keeper between the secured position and the released position;

wherein the keeper includes a groove arranged to receive both the first portion and the second portion of the base during operation of the retainer in the engaged configuration.

20. A harness assembly for use with a patient transport apparatus, the harness assembly comprising:

a strap for securing a patient to the patient transport apparatus, the strap defining a distal end with a strap interface for attaching to the patient transport apparatus, and a proximal end;

a guard configured for removable attachment to the proximal end of the strap, the guard including:

a base defining a channel arranged to receive the proximal end of the strap therein;

a keeper arranged for movement relative to the base between:

a released position to permit movement of the proximal end of the strap along the channel of the base, and a secured position to restrict movement of the proximal end of the strap out of the channel; and a retainer coupled between the base and the keeper and being operable between:

an engaged configuration to retain the keeper in the secured position, and a disengaged configuration to permit movement of the keeper between the secured position and the released position; and a tether lock configured to operate in a locked configuration where the tether lock secures a portion of the strap, wherein the tether lock includes a latch and a catch arranged to secure the latch to at least partially limit movement of the latch relative to the catch during operation of the tether lock in the locked configuration.

* * * * *